United States Patent [19]
Webster et al.

[11] Patent Number: 5,824,536
[45] Date of Patent: Oct. 20, 1998

[54] INFLUENZA VIRUS REPLICATED IN MAMMALIAN CELL CULTURE AND VACCINE PRODUCTION

[75] Inventors: Robert G. Webster, Memphis, Tenn.; Nicolai V. Kaverin, Moscow, Russian Federation

[73] Assignee: St. Jude Children's Research Hospital, Memphis, Tenn.

[21] Appl. No.: 664,783

[22] Filed: Jun. 17, 1996

Related U.S. Application Data

[63] Continuation of Ser. No. 628,384, Apr. 5, 1996, abandoned, which is a continuation-in-part of Ser. No. 340,254, Nov. 16, 1994, abandoned, which is a continuation-in-part of Ser. No. 294,644, Aug. 23, 1994, abandoned.

[51] Int. Cl.$^6$ .............................. C12N 5/00; C12N 7/02; C12N 7/00
[52] U.S. Cl. ...................... 435/235.1; 435/239; 435/325
[58] Field of Search ........................... 435/235.1, 239.325

[56] References Cited

U.S. PATENT DOCUMENTS 4,500,513  2/1985  Brown et al. .

OTHER PUBLICATIONS

Baum, L. G. and J. C. Paulson, "Sialyloligosaccharides of the respiratory epithelium in the selection of human influenza virus receptor specificty," *Acta Histochemica Supplementband XL*:35–38 (1990).

Demidova, S. A. et al., "Isolation and Study of Influenza A Virus in Varying Cell Cultures," *Vopr. Virusol.* 0(4):346–352 (1979).

Frank, A. L. et al., "Comparison of Different Tissue Cultures for Isolation and Quantitation of Influenza and Parainfluenza Viruses," *J. Clin. Microbiol.* 10(1):32–36 (1979).

Govorkova, E. A. et al., "Replicaiton of Influenza A Viruses in a Green Monkey Kidney Continuous Cell Line (Vero)," *J. Infect. Dis.* 172:250–253 (Jul. 1995).

Grachev, V. P. et al., "Comparison of Methods for Large–Scale Propagation of Cells and Viruses," *Vopr. Virusol.* 0(4):44–49 (1983).

Grachev, V. P., "World Health Organization Attitude concerning the Use of Continuous Cell Lines as Substrates for Production of Human Virus Vaccines," in:*Viral Vaccines*, Mizrahi, A. ed., Wiley–Liss, New York, N. Y.:37–67 (1990).

Gubareva, L. V. et al., "Codominant Mixtures of Viruses in Reference Strains of Influenza Virus Due to Host Cell Variation," *Virol.* 199(1):89–97 (Feb. 1994).

Hayden, F. G. et al., "Plaque Inhibition Assay for Drug Susceptibility Testing of Influenza Viruses," *Antimicrob. Agents Chemother.* 17(5):865–870 (1980).

Hayflick, L., "History of Cell Substrates Used for Human Biologicals," *Develop. Biol. Stand.* 70:11–26 (1988).

Hinshaw, V. S. et al., "Apoptosis: a Mechanism of Cell Killing by Influenza A and B Viruses," *J. Virol.* 68(6):3667–3673 (Jun. 1994).

Itoh, H. et al., "Effect of Trypsin on Viral Susceptibility of Vero Cell Cultures—Cercopithecus Kidney Line," *Japan. J. Med. Sci. Biol.* 23(4):227–235 (1970).

Itoh, H., et al., "Viral Susceptibility of an African Green Monkey Kidney Cell Lline–Vero," *Virus* 18(3):10–24 (1968).

Katz, J. M. and R. G. Webster, "Antigenic and Structural Characterizaiton of Multiple Subpopulations of H3N2 Influenza Virus from an Individual," *Virol.* 165(2):446–456 (1988).

Katz, J. M. and R. G. Webster, "Efficacy of Inactivated Influenza A Virus (H3N2) Vaccines Grown in Mammalian Cells or Embryonated Eggs," *J. Infect. Dis.* 160(2):191–198 (1989).

Katz, J. M. and R. G. Webster, "Amino acid sequence identity between the HA1 of influenza A (H3N2) viruses grown in mammalian and primary chick kidney cells," *J. Gen. Virol.* 73(5):1159–1165 (1992).

Katz, J. M. et al., "Host Cell–Mediated Variation in H3N2 Influenza Viruses," *Virol.* 156(2):386–395 (1987).

Katz, J. M. et al., "Direct Sequencing of the HA Gene of Influenza (H3N2) Virus in Original Clinical Samples Reveals Sequence Identity with Mammalian Cell–Grown Virus," *J. Virol.* 64(4):1808–1811 (1990).

Kaverin, N. V. and R. G. Webster, "Impairment of Multicycle Influenza Virus Growth in Vero (WHO) Cells by Loss of Trypsin Activity," *J. Virol.* 69(4):2700–2703 (Apr. 1995).

Kerr, A. A. et al., "Gastric Flu: Influenza B Causing Abdominal Symptoms in Children," *Lancet* 1(7902):291–295 (1975).

Kodihalli, S. et al., "Selection of a Single Amino Acid Substitution in the Hemagglutinin Molecule by Chicken Eggs Can Render Influenza A Virus (H3) Candidate Vaccine Ineffective," *J. Virol.* 69(8):4888–4897 (Aug. 1995).

Lau, S. C. and C. Scholtissek, "Abortive Infection of Vero Cells by an Influenza A Virus (FPV)," *Virol.* 212(1):225–231 (Sep. 1995).

Montagnon, B. J., "Polio and Rabies Vaccines Produced in Continuous Cell Lines: A Reality for Vero Cell Line," *Develop. Biol. Stand.* 70:27–47 (1989).

Monto, A. S. et al., "Relative Efficacy of Embryonated Eggs and Cell Culture for Isolation of Contemporary Influenza Viruses," *J. Clin. Microbiol.* 13(1):233–235 (1981).

(List continued on next page.)

*Primary Examiner*—Leon B. Lankford, Jr.
*Attorney, Agent, or Firm*—Sterne, Kessler, Goldstein & Fox P.L.L.C.

[57] ABSTRACT

The invention provides replication of high growth influenza virus strains, derived from clinical isolates, in cultured mammalian cells by infecting the mammalian cells with the high growth strains to obtain infected cells, and culturing the cells while maintaining a trypsin concentration range of 0.05–1.0 µg/ml in the culture medium, where the resulting replicated virus is suitable for use in mammalian influenza vaccines and vaccination methods, which are also provided by the invention.

12 Claims, 4 Drawing Sheets

OTHER PUBLICATIONS

Nakamura, K. and M. Homma, "Protein Synthesis in Vero Cells Abortively Infected with Influenza B Virus," *J. Gen. Virol* 56(*1*):199–202 (1981).

Ogra, P. L. et al., "Clinical and Immunologic Evaluation of Neuraminidase–Specific Influenza A Virus Vaccine in Humans," *J. Infect. Dis.* 135(*4*):499–506 (1977).

Oxford, J. S. et al., "Direct isolation in eggs of influenza A (H1N1) and B viruses with haemagglutinins of different antigenic and amino acid composition," *J. Gen. Virol.* 72(*1*):185–189 (1991).

Oxford, J. S. et al., "A host–cell–selected variant of influenza B virus with a single nucleotide substitution in HA affecting a potential glycosylation site was attenuated in virulence for volunteers," *Arch. Virol.* 110:37–46 (1990).

Robertson, J. S. et al., "Alterations in the Hemagglutinin Associated with Adaptation of Influenza B Virus to Growth in Eggs," *Virol.* 143(*1*):166–174 (1985).

Robertson, J. S. et al., "The Hemagglutinin of Influenza B Virus Present in Clinical Material Is a Single Species Identical to That of Mammalian Cell–Grown Virus," *Virol.* 179(*1*):35–40 (1990).

Robertson, J. S. et al., "High Growth Reassortant Influenza Vaccine Viruses: New Approaches to their Control," *Biologicals* 20(*3*):213–220 (1992).

Schepetiuk, S. K. and T. Kok, "The use of MDCK, MEK and LLC–MK2 cell lines with enzyme immunoassay for the isolation of influenza and parainfluenza viruses from clinical specimens," *J. Virol. Meth.* 42:241–250 (1993).

Smith, C. D. et al., "Alternative Cell Line for Virus Isolation," *J. Clin. Microbiol.* 24(*2*):265–268 (1986).

Takizawa, T. et al., "Induction of programmed cell death (apoptosis) by influenza virus infection in tissue culture cells," *J. Gen. Virol.* 74(*11*):2347–2355 (Nov. 1993).

Valette, M. et al., "Susceptibilities to Rimantadine of Influenza A/H1N1 and A/H3N2 Viruses Isolated during the Epidemics of 1988 to 1989 and 1989 to 1990," *Antimicrob. Agents Chemother.* 37(*10*):2239–2240 (Oct. 1993).

Wood, J. M. et al., "Influenza A (H1N1) Vaccine Efficacy in Animal Models is Influenced by Two Amino Acid Substitutions in the Hemagglutinin Molecule," *Virol.* 171(*1*):214–221 (1989).

WHO Expert Committee on Biological Standardization, TRS No. 673 (1982).

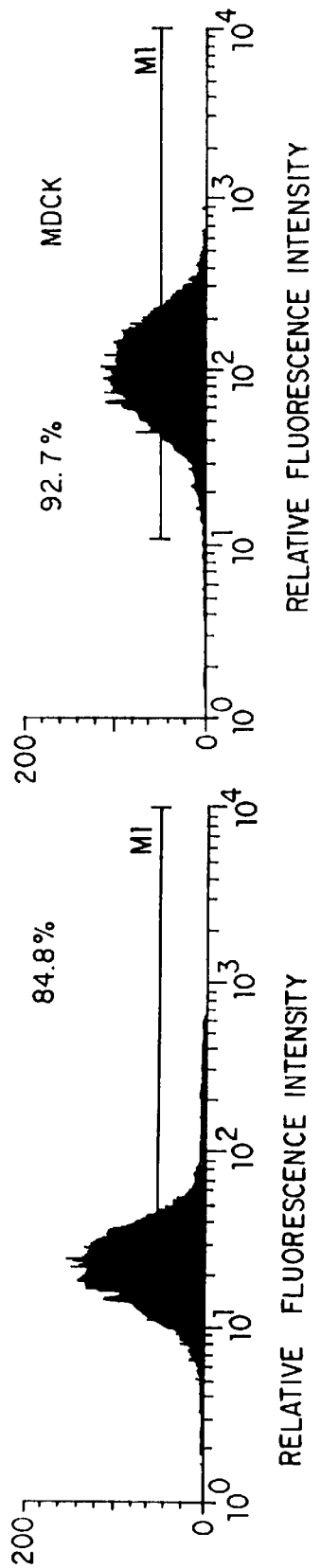

INFLUENZA VIRUS REPLICATED IN MAMMALIAN CELL CULTURE AND VACCINE PRODUCTION

This application is a continuation of U.S. application Ser. No. 08/628,384, filed Apr. 5, 1996, now abandoned, which is a continuation-in-part of U.S. application Ser. No. 08/340, 254, filed Nov. 16, 1994, now abandoned which is a continuation-in-part of U.S. application Ser. No. 08/294, 644, filed Aug. 23, 1994, now abandoned.

BACKGROUND OF THE INVENTION

1. Field of the Invention

The present invention, in the fields of virology and vaccine production, relates to replicated mammalian influenza viruses, grown in mammalian cell culture, which are suitable for use in mammalian influenza virus vaccine production. The replicated viruses are obtained from high growth strains of (i) reassortants between high growth master donor strains and clinical isolates, or (ii) passaged clinical isolates. The infected cell culture uses a low concentration range of trypsin (0.05–1.0 $\mu$g/ml), continuously present in the medium, to provide high titers of the replicated virus. The invention also relates to methods for making and using such replicated viruses, such as for vaccine compositions and for vaccination methods.

2. Related Art

For the past several decades, fertilized chicken eggs have been used as a host system to replicate human influenza viruses with infectivity titers sufficient for use in vaccine production. Clinical isolates of human influenza virus are taken from infected patients and are reassorted in embryonated chicken eggs with laboratory-adapted master strains of high-growth donor viruses. The purpose of this reassortment is to increase the yield of candidate vaccine strains achieved by recombining at least the HA and NA genes from the primary clinical isolate isolates, with the internal genes of the master strain donor viruses. The high growth reassortant vaccine strains must also not contaminated with genes coding for antigenic determinants of the laboratory adapted viruses. This provides high growth reassortants having antigenic determinants similar to those of the clinical isolates. (Robertson et al., *Biologicals* 20:213–220 (1992)). The reassorted influenza virus is then grown in embryonated chicken eggs, purified from virus-containing allantoic fluid of the eggs and subsequently inactivated for use as vaccines.

However, a large body of data now suggests that this is a problematic system because of the frequency of viral mutation in antigenic sites of the major virus glycoprotein, hemagglutinin (HA), during replication in the chicken eggs. Even a single passage of a human influenza virus isolate or reassortant in chicken eggs leads to the selection of viral variants that differ in their antigenic determinants from those of the original clinical isolates. For example, the cultivation of influenza A and B viruses in chicken eggs often leads to the selection by the host system of variants having antigenic and structural changes in the viral HA molecule, making the variants ineffective or significantly less effective when used in an influenza vaccine (Kodihalli et al., *J Virol.* 69:4888–4897 (1995); Gubareva et al., *Virol.* 199:89–97 (1994); Katz & Webster, *J Infect. Dis.* 160:191–198 (1989); Wood et al., *Virol.* 171:214–221 (1989); Katz et al., Virology 156:386–395 (1987); Robertson et al., *Virology* 143:166–174 (1985)). In addition, the replicative properties of egg-grown viruses are not as consistent with natural infection as those of viruses grown in mammalian cells (Katz et al., *J Virol.* 64:1808–1811 (1990); Robertson et al., *Virology* 179:35–40 (1990)).

Additionally, embryonated chicken eggs have potentially serious limitations as a host system, e.g., due to the lack of reliable year-around supplies of high-quality eggs and the low susceptibility of summer eggs to influenza virus infection (Monto, et al., *J. Clin. Microb.* 13:233–235 (1981)). Furthermore, the presence of adventitious agents in eggs can jeopardize the preparation of live-attenuated influenza virus vaccines. Adventitious agents are infectious contaminants (such as other viruses) in host systems that make them unsuitable or uncertifiable for use in vaccine production.

Cultured mammalian cells have also been used for virus replication and have been classified into at least two distinct groups. Primary diploid cells are those derived from intact tissue and have not been subcultivated. Continuous cell lines (CCLs) are cultured primary cells that replicate indefinitely and may be capable of growth in suspension culture. Haylick, in *Continuous Cell Lines as Substrates for Biologicals*, Arlington, Va., p. 2 (1988).

At present, many viral vaccines other than influenza are produced using primary trypsinized cells, including cells from monkey kidneys, and the kidneys of rabbits and hamsters. Primary diploid cell cultures have certain advantages such as easy preparation using simple media and bovine sera and sensitivity to a wide-range multiple viruses. However, primary diploid cells suffer from disadvantages, such as contamination by various adventitous agents, variable quality and sensitivity; and difficulty in obtaining suitable tissue for cultivation (e.g., monkey kidneys).

For example, primary diploid cell cultures obtained from monkey kidneys of wild animals usually contain endogenous viruses (Grachev, In Burgasov; ed., "*Guidance for the Production of Vaccines and Sera*." Medicine, Moscow, p 176 (1978)). The number of adventitous agents depends on many factors, such as the methods of isolation, the cell systems used, the number of passages, the time of incubation and co-cultivation. The frequency of isolation of viruses from primary diploid cell cultures of monkey kidneys is directly proportional to the incubation period of the cells. Grachev, In *Zh. Microbiol. Epidemiol. Immunobiol.* 2:76 (1987).

In contrast, the advantages of using continuous cell lines are their retention of original antigenic characteristics of the infected virus; standardization, high susceptibility to variants of the same virus, and ability to be grown as a large mass of cells using microcarrier or suspension fermentor systems.

However, these advantages themselves do make such cell lines suitable for use in vaccine production. Mizrahi, ed., *Viral Vaccines*, Wiley-Liss, New York (1990), pp. 39–67. For example, influenza A viruses isolated and passaged exclusively in mammalian cell cultures have been found in some cases to retain most or all of their original antigenic characteristics, a feature that would prove highly advantageous in vaccine production. (Katz et al., *Virology* 165:446–456 (1988); Robertson et al., *Virology* 179:35–40 (1990); Katz et al.,*J. Infect. Dis.* 160:191–198 (1989); Wood et al., *Virology* 171:214–221 (1989)).

However, mammalian primary diploid cell cultures present difficulties as a host system for vaccine production. This is due to problems such as contamination of the cell culture with adventitious agents, variable quality of the cells in the cell culture, different sensitivities of the cells to variants of the same virus, low virus titers and the high cost and difficulties in obtaining and preparing such cell cultures.

In another example, although human diploid (MRC-5) cells can support the growth of influenza viruses, such systems have stringent growth media requirements making them suboptimal for large-scale production of influenza viruses for use in vaccines.

Furthermore, only MDCK cells, among the continuous cell lines tested, have been reported to support potentially sufficient growth and isolation of viruses (Frank et al., *J. Clin. Microb.* 10:32–36 (1979); Schepetink & Kok, *J. Virol. Methods* 42:241–250 (1993)). However, this line has been found to produce tumors and has thus not been certified for vaccine production, as not substantially free of adventitious agents.

Two other continuous cell lines—African green monkey kidney (Vero) cells and baby hamster kidney (BK-21)—are characterized, approved and certified by the World Health Organization (WHO) for production of human vaccines. However, Vero cells, while certified, were previously found unsuitable for large-scale production of human influenza virus vaccines. For example, the growth of influenza B in Vero cells was greatly restricted as compared to MDCK cells (Nakamura et al., *J. Gen. Virol.* 56:199–202 (1981)). Additionally, attempts to use Vero cells to evaluate the rimantadine sensitivity of human H1N1 and H3N2 influenza A viruses gave ambiguous results, due to the low titers of viruses produced in these cells, as compared with MDCK cells (Valette et al., *Antimicrobiol. Agent and Chemotherapy* 37:2239–2240 (1993)).

Thus, these and other studies indicate that influenza viruses have not previously replicated well in Vero cells, making them unsuitable for large-scale vaccine production. (Demidova et al., *Vopr. Virosol* (Russian) 346–352 (1979); Lau & Scholtissek, *Virology* 212:225–231 (1995)).

Itoh et al., *Japan J. Mol. Sci. Biol.* 23:227–235 (1970) discloses a study of Vero cell cultures for infection with parainfluenza and influenza A viruses using a final added trypsin concentration of 1.5–1.8 µg/ml. Itoh used chicken egg-grown viruses (Itoh et al. *Virus* 18:214–226 (1968)) to infect Vero cells under the above conditions, and found enhanced viral titers (over non-trypsin containing medium) for some of the influenza A strains tested, but Itoh could not demonstrate enhanced viral titers for influenza B strains.

Influenza viruses have eight negative-sense RNA (nsRNA) gene segments that encode at least 10 polypeptides, including RNA-directed RNA polymerase proteins (PB2, PB1 and PA), nucleoprotein (NP), neuraminidase (NA), hemagglutinin (HA, active with cleavage and association of subunits HA1 and HA2), the matrix proteins (M1 and M2) and the non-structural proteins (NS1 and NS2) (Krug et al., "Expression and Replication of the Influenza Virus Genome," in *The Influenza Viruses*, R. M. Krug, ed., Plenum Press, New York (1989), pp. 89–152).

Influenza viruses are enclosed by lipid envelopes, derived from the plasma membrane of the host cell. The HA and NA proteins are the primary antigenic determinants and are embedded in the viral envelope by sequences of hydrophobic amino acids (Air et al., *Structure, Function, and Genetics* 6:341–356 (1989); Wharton et al., "Structure, Function, and Antigenicity of the Hemagglutinin of Influenza Virus" in *The Influenza Viruses*, R. M. Krug, ed., Plenum Press, New York (1989), pp. 153–174).

The major influenza virus glycoprotein, HA, is synthesized in infected cells as a single polypeptide. Post-translational protease cleavage of the precursor HA results in the formation of the two subunits, HA1 and HA2, joined by a disulfide bond. Cleavage is essential for production of infectious viruses: virions containing uncleaved HA are noninfectious. The cleavage process can occur intracellularly or extracellularly. While HAs of infectious viruses are cleaved by extracellular proteases, such as from intestinal bacteria or the pancreas in vivo, the HAs of human, swine and most avian influenza virus strains cannot be cleaved by intracellular proteases. Therefore, replication of these viruses in many cell cultures requires the addition of a protease (such as trypsin) to the maintenance medium to ensure HA cleavage, thereby permitting activation of the progeny virus so that the rounds of infection can continue. Previous publications have suggested using a trypsin concentration in the range of 4–25 µg/ml (U.S. Pat. No. 4,500, 513). Vero cells were recently discovered to produce an activity that inactivates exogenous trypsin (Kaverin & Webster, *J. Virol.* 69:2700–2703 (1995)).

The background art has thus established a long-felt need for a method of influenza virus and vaccine production in a host cell system that improves on the use of chicken eggs. Such a host system would maintain antigenic properties of the clinical isolates of the natural virus and provide high titers of replicated virus, without having significant adventitious agents which are unsuitable for vaccine production.

SUMMARY OF THE INVENTION

The present invention includes methods, replicated viruses and vaccine compositions using high growth strains of mammalian influenza viruses, passaged from, or reassorted with, viral clinical isolates. The high growth strains of the invention can be reassortants made with laboratory high growth master donor strains, or they can be isolates that have been passaged in primary cell culture and selected for high growth. These methods use mammalian host cells that are infected with the high growth strains and then cultured with a continuous and low trypsin concentration in the culture medium. The methods provide replicated virus having high infectivity titers. These replicated, high growth strains are suitable for, and included in, influenza virus vaccines of the invention, for which the replicated virus is inactivated and/or attenuated.

The invention thus provides replicated influenza viruses and vaccines that comprise at least one replicated influenza virus strain, where the vaccine contains the replicated virus in an inactivated or attenuated form. These vaccines have substantially similar antigenicity to the viral clinical isolates, relative to chicken egg-grown viruses, where selection pressures in the eggs change the viruses' antigenicity from that of the clinical isolates, such as through mutation of the HA gene.

In contrast to influenza viruses grown in other host cell types, such as chicken eggs, replicated influenza viruses and vaccines of the present invention provide at least one of: (i) substantially similar antigenicity to the clinical isolate; (ii) consistently high titers; (iii) lack of contamination by adventitious agents; (iv) consistent cell growth qualities; and (v) relatively less cost and technical difficulties in host cell replication.

Influenza virus vaccines of the invention can include at least one replicated virus strain (e.g., 1–50 strains) of a mammalian influenza virus A or B. Preferably the mammal host cells are continuous cell cultures of primary, cultured epithelial cells or fibroblasts, as mammalian cell lines of passage number 10–250. Preferably used for vaccine production are primary Vero cells as a continuous cell culture of a passage number of about 20–250. Currently available and certified (e.g., by the World Health Organization, WHO). Vero cell lines are passage number 135–190 (e.g., ATTC NO:X38).

Replicated influenza virus of the invention, in isolated, purified or concentrated form, preferably has an infectivity titer of about $10^6$–$10^9$ (such as $10^6$–$10^7$, $10^7$ and $10^8$–$10^9$, or any range or value therein) plaque forming units (PFU) per ml.

It is now discovered that providing a continuous, low trypsin concentration in the cell culture can circumvent the problem of trypsin inactivation or viral replication inhibition found previously in mammalian cell cultures. Such trypsin concentrations are also discovered to ensure multicycle replication that is comparable, in some or all respects, to that seen with either human influenza A or B viruses grown in chicken eggs.

The present invention also provides vaccine compositions comprising at least one strain of a replicated influenza virus of the present invention, in inactivated or attenuated form, optionally further comprising at least one of: (a) at least one pharmaceutically acceptable carrier or diluent; (b) at least one adjuvant and/or (c) at least one viral chemotherapeutic agent. The at least one carrier, diluent, adjuvant or chemotherapeutic agent enhances at least one immune response to at least one pathogenic influenza virus in a mammal administered the vaccine composition.

The present invention also provides a method for eliciting an immune response to at least one influenza virus strain in a mammal, which response is prophylactic or therapeutic for an influenza virus infection. The method comprises administering to the mammal a vaccine composition comprising an inactivated and/or attenuated, replicated influenza virus of the present invention. The composition is provided in an amount that is protective or therapeutic for the mammal against a clinical influenza virus pathology caused by infection with at least one influenza A or B virus strain.

Other objects, features, advantages, utilities and embodiments of the present invention will be apparent to skilled practitioners from the following detailed description and examples relating to the present invention.

BRIEF DESCRIPTION OF THE FIGURES

FIG. 1A–D: Analysis of the abundance of sialic acid (SA) α2,3-Galactose (Gal), and SAα2,6-Gal linkages on the surface of Vero and MDCK cells. The profile shown depicts cell number as a function of the log of relative fluorescence intensity of SAα2,3-Gal-α(2,3; *Maackia amurensis* agglutinin) and SAα2, 6-Gal α(2, 6; *Sambucus nigra* agglutinin)—specific lectin-reactive oligosaccharide expression on the surface of: Vero cells (FIGS. 1A–1B) and MDCK cells (FIGS. 1C–1D).

DETAILED DESCRIPTION OF THE PREFERRED EMBODIMENTS

Figure 2A:
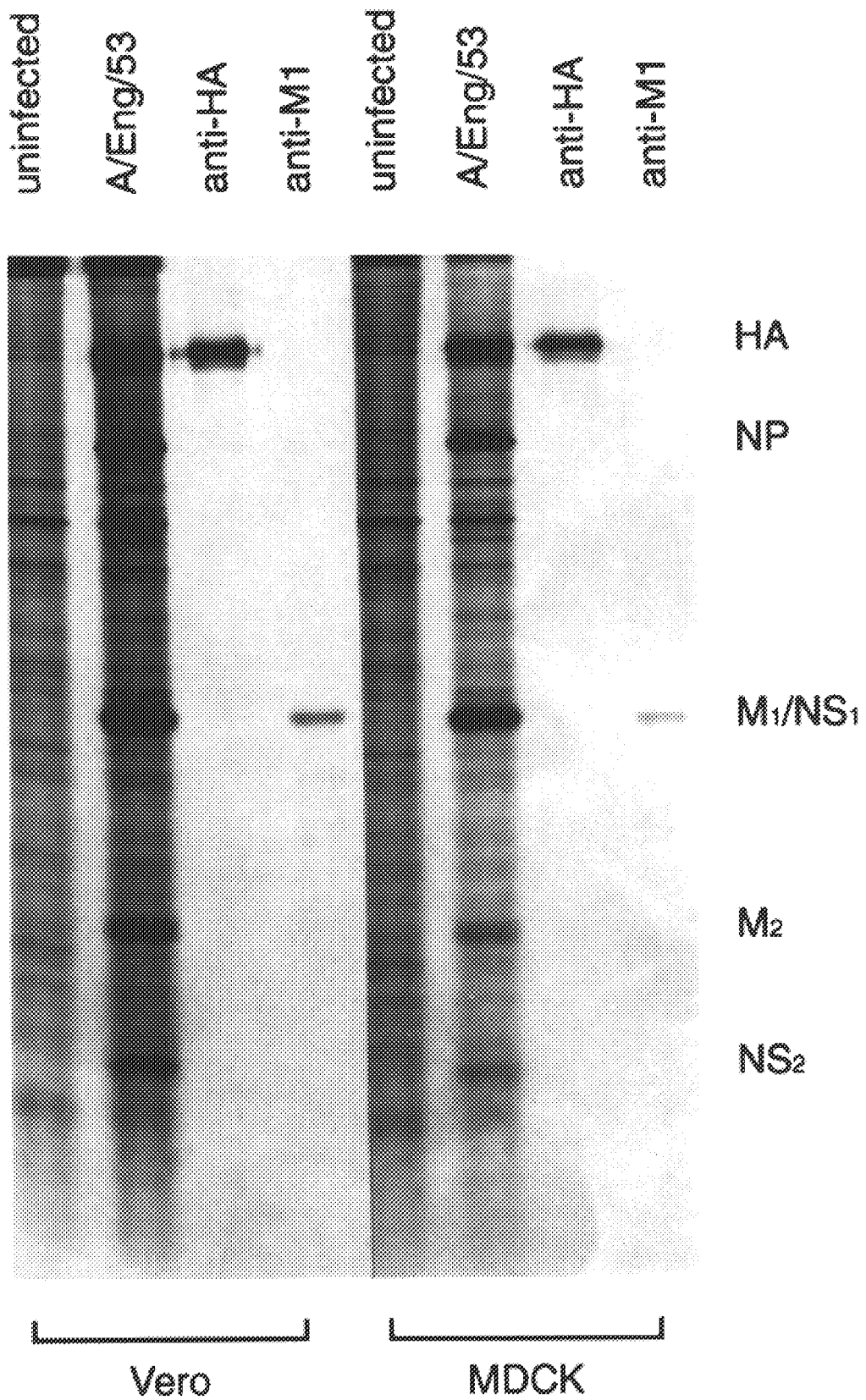
FIGS. 2A–B. Protein synthesis in Vero and MDCK cells infected with (FIG. 2A) influenza A/England/1/53 (H1N1) or (FIG. 2B) influenza B/Ann Arbor/1/86 viruses. Vero or MDCK cells were infected with either influenza A or B viruses at a multiplicity of infection (m.o.i.) of ~30 PFU/cell. After absorption for 1 hour at 37° C., the cells were washed and incubated for 5 hours (for influenza A virus) or 7 hours (for influenza B virus). Thereafter the cells were radioactively labeled with Tran($^{35}$S)methionine/cysteine (100 μCi/ml) for 2 hours at 37° C. Cells were washed, lysed and immunoprecipitated with specific monoclonal antibodies against HA, NP, M1, M2 and NS1 proteins. Uninfected cells, cells infected with either influenza A strain (FIG. 2A) or B strain (FIG. 2B) and cell precipitates were analyzed by SDS-PAGE. The positions of viral proteins HA, NP, M1, NS1, M2 and NS2 are indicated.

The present invention provides replicated influenza virus using continuous cell lines of cultured mammalian primary cells, in media having a low continuous trypsin concentration. The viruses used for generating the replicated virus are high growth strains of clinical isolates of at least one mammalian influenza virus strain. The high growth strains are selected from passaged or reassorted clinical isolates. The use of low trypsin concentrations (e.g., 0.05–1.0 μg/ml) is unexpectedly discovered to provide high infectivity titers of replicated influenza virus having substantially similar antigenicity to that of the clinical isolates, where the host cells and replicated viruses are suitable for use in influenza virus vaccine production. Such replicated viruses have improved antigenic stability as compared with viruses grown in embryonated chicken eggs, while also being certifiable for human vaccine production.

The term "high growth" as used in the literature can be ambiguous as it can refer to either high HA titers or high infectivity titers, assayed in either eggs or tissue culture. In the context of the present invention, "high growth" viruses are defined to produce high infectivity titers in in vitro tissue culture replication systems, such as $10^5$–$10^{10}$ PFU/ml, and preferably $10^6$–$10^9$ PFU/ml.

The screening of influenza viruses for use in replication or vaccine production, can be assayed using any known and/or suitable assay, as is known in the art. Such assays (alone or in any combination) that are suitable for screening include, but are not limited to, viral replication, quantitative and/or qualitative measurement of inactivation (e.g., by antisera), transcription, replication, translation, virion incorporation, virulence, HA or NA activity (HA activity preferred), viral yield, and/or morphogenesis, using such methods as reverse genetics, reassortment, complementation, and/or infection. For example, virus replication assays can be used to screen for attenuation or inactivation of the virus. See, e.g., Krug, R. M., ed., *The Influenza Viruses*, Plenum Press, New York, (1989).

For culturing mammalian host cells used for viral replication in methods of the present invention, a trypsin concentration between 0.05 and 1.0 μg/ml (e.g., 0.05–0.09, 0.1–0.2, 0.2–0.5, 0.6–0.9, 0.7–0.9, 0.8–1.0 or any range or value therein) can be used during the host cell growth cycle and/or viral growth cycle, by adding trypsin continuously or at intervals to the culture medium. The multiplicity of infection of the virus for the host cell culture can be from $1\times10^{-6}$ TCID$_{50}$ to $5\times10^{-3}$ TCID$_{50}$ per cell (e.g., $1\times10^{-6}$ TCID$_{50}$ to $1\times10^{-5}$ TCID$_{50}$, $2\times10^{-5}$ TCID$_{50}$ to $1\times10^{-4}$ TCID$_{50}$, or $2\times10^{-4}$ TCID$_{50}$ to $5\times10^{-3}$ TCID$_{50}$, or any range or value therein. "TCID$_{50}$" stands for the tissue culture infective dose, or the dose sufficient to infect 50% of the cells.

Cell Lines and Influenza Viruses That Can Be Used in the Present Invention

According to the present invention, any clinical isolate of at least one strain of a mammalian influenza A or B virus can be used to obtain high growth strains suitable for replicating in mammal host cells, in order to provide replicated influenza virus of the invention. The clinical isolate can be made into a high growth strain by reassortment with a high growth master donor strain, or by multiple passages of the clinical isolate in continuous mammalian cell lines, with selection of high growth variants.

The clinical isolates are preferably reassorted with laboratory high growth master donor strains in culture, and the reassortants selected that have HA and NA genes from the isolates, and internal genes from the high growth master laboratory strains. For example, the resulting strain for the influenza A component can be a reassortant virus that contains internal genes from the master donor strain A/PR/8/34 (H1N1), which provides high growth in host cells, as well as at least the HA gene coding for at least one surface antigen of the clinical isolate of the influenza virus (using known methods, e.g., according to Robertson et al., *Biologicals* 20:213–220 (1992)). Such reassortants can be made more rapidly than high growth strains made by multiple passages of the clinical isolates.

A high growth virus strain, derived from the clinical isolate strain or a reassortant thereof, is then replicated in suitable mammalian host cells in the continuous presence of a trypsin concentration of 0.05–1.0 µg/ml, to obtain sufficiently high infectivity titers (e.g., $10^6$–$10^9$ PFU/ml) that are useful for vaccine production.

Cell Lines

According to methods for replicating viruses of the present invention, suitable mammalian host cells can be used, including Vero cells or other mammalian cells suitably excluding adventitious agents, preferably of a suitable passage number that can be certified according to the WHO requirements for vaccine production (Mizrahi, ed., *Viral Vaccines*, Wiley-Liss, New York (1990), pp. 39–60). Non-limiting examples of cell lines that can be suitable for methods, viruses and compositions used in the present invention, include, but are not limited to, mammalian fibroblast or cultured epithelial cells as continuous cell lines. Further non-limiting examples include Vero, MDBK, BK-21 and CV-1 cells, readily available from commercial sources (e.g., ATCC, Rockville, Md.). Vero cells of passage number less than 191 are preferred, or any range or value therein.

Continuous Cell Lines

Continuous cell lines (CCLs), derived from primary diploid cells, are preferred for replicating influenza virus according to the present invention. CCLs possess advantages over primary diploid cells, such as suitability for the large-scale cultivation; high sensitivity to different viral variants; unrestricted and stable growth; and low cost (relative to primary diploid cell cultures). Montagnon et al., *Dev. Biol. Stand.* 47:55 (1987); Grachev, *Virol.* 4:44 (1983); Smith et al., *J. Clin. Microbiol.* 24:265 (1986); Grachev et al., in *Guidance for the Production of Vaccines and Sera*, Burgamov, ed., Medicine, Moscow p. 176 (1978)).

WHO certified, or certifiable, continuous cell lines are preferred for producing influenza virus vaccines of the present invention. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the CLLs are free from detectable adventitious agents. In some countries, karyology may also be required. In addition, tumorigenicity is preferably tested in cells that are at the same passage level as those used for vaccine production. The replicated virus is preferably purified by a process that has been shown to give consistent results, before being inactivated or attenuated for vaccine production (see, e.g., World Health Organization TRS No. 673 (1982)).

It is preferred to establish a complete characterization of the continuous cell line to be used, so that appropriate tests for purity of the final product can be included. Data that can be used for the characterization of a continuous cell line to be used in the present invention includes (a) information on its origin, derivation, and passage history; (b) information on its growth and morphological characteristics; (c) results of tests of adventitious agents; (d) distinguishing features, such as biochemical, imunological, and cytogenetic patterns which allow the cells to be clearly recognized among other cell lines; and (e) results of tests for tumorigenicity. Preferably, the passage level, or population doubling, of the cell line used is as low as possible.

It is preferred that the replicated virus produced in continuous cell lines is highly purified prior to vaccine formulation according to the invention. Generally, the purification procedures will result in the extensive removal of cellular DNA, other cellular components, and adventitious agents. Procedures that extensively degrade or denature DNA can also be used. See, e.g., Mizrahi, ed., *Viral Vaccines*, Wiley-Liss, New York pp. 39–67 (1990).

Vaccines

The resulting replicated virus can then be concentrated and/or purified (e.g., by centrifugation or column chromatography) and then inactivated or attenuated using known method steps.

Inactivated Vaccines. Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccine or subvirion (SV) virus vaccine. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., *J. Infect. Dis.* 135:499–506 (1977)). Inactivated vaccines containing both relevant surface antigens are preferred.

Live Attenuated Virus Vaccines. Live, attenuated influenza virus vaccines, using replicated virus of the invention, can also be used for preventing or treating influenza virus infection, according to known method steps: Attenuation is preferably achieved in a single step by transfer of attenuating genes from an attenuated donor virus to a replicated isolate or reassorted virus according to known methods (see, e.g., Murphy, *Infect. Dis. Clin. Pract.* 2:174–181 (1993)). Since resistance to influenza A virus is mediated by the development of an immune response to the HA and NA glycoproteins, the genes coding for these surface antigens must come from the reassorted viruses or high growth clinical isolates. The attenuating genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, *J. Infect. Dis.* 169:68–76 (1994); Murphy, *Infect. Dis. Clin. Pract.* 2:174–181 (1993)). Additionally, live, attenuated reassortant virus vaccines can be generated by mating the ca donor virus with a virulent replicated virus of the invention. Reassortant progeny are then selected at 25° C. (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as-well as into coding regions. Such attenuating mutations can also be introduced into genes other than the HA or NA, e.g., the PB2 polymerase gene (Subbarao et al., *J. Virol.* 67:7223–7228 (1993)). Thus, new donor viruses can also be generated bearing attenuating mutations introduced by site-directed mutagenesis, and such new donor viruses can be used in the production of live attenuated reassortants H1N1 and H3N2 vaccine candidates in a manner analogous to that described above for the A/AA/6/60 ca donor virus. Similarly, other known and suitable attenuated donor strains can be reassorted with replicated influenza virus of the invention to obtain attenuated vaccines suitable for use in the vaccination of mammals. (Ewami et al., *Proc. Natl. Acad. Sci. USA* 87:3802–3805 (1990); Muster et al., *Proc. Natl. Acad. Sci. USA* 88:5177–5181 (1991); Subbarao et al., *J. Virol.* 67:7223–7228 (1993); U.S. patent application Ser. No. 08/471,100, which references are entirely incorporated by reference)

It is preferred that such attenuated viruses maintain the genes from the replicated virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal chance of inducing a serious pathogenic condition in the vaccinated mammal.

The replicated virus can thus be attenuated or inactivated, formulated and administered, according to known methods, as a vaccine to induce an immune response in a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., *Giornale di Igiene e Medicina Preventiva* 29.4–58 (1988); Kilbourne, *Bull.* M2 *World Health Org.* 41:643–645 (1969); Aymard-Henry et al., *Bull. World Health Org.* 481:199–202 (1973); Mahy et al., *J. Biol. Stand.* 5:237–247 (1977); Barrett et al., *Virology: A Practical Approach*, Oxford IRL Press, Oxford, pp. 119–150 (1985); Robertson et al., *Biologicals* 20:213–220 (1992).

Pharmaceutical Compositions

Pharmaceutical compositions of the present invention, suitable for inoculation or for parenteral or oral administration, comprise attenuated or inactivated mammalian influenza viruses, optionally further comprising sterile aqueous or non-aqueous solutions, suspensions, and emulsions. The composition can further comprise auxiliary agents or excipients, as known in the art. See, e.g., Berkow et al., eds., *The Merck Manual*, 15th edition, Merck and Co., Rahway, N.J. (1987); Goodman et al., eds., *Goodman and Gilman's The Pharmacological Basis of Therapeutics*, 8th edition, Pergamon Press, Inc., Elmsford, N.Y. (1990); *Avery's Drug Treatment: Principles and Practice of Clinical Pharmacology and Therapeutics*, 3rd edition, ADIS Press, LTD., Williams and Wilkins, Baltimore, Md. (1987); Osol, A., ed., *Remington's Pharmaceutical Sciences*, Mack Publishing Co, Easton, Pa. pp. 1324–1341 (1980); Katzung, ed. *Basic and Clinical Pharmacology*, Fifth Edition, Appleton and Lange, Norwalk, Conn. (1992), which references and references cited therein, are entirely incorporated herein by reference as they show the state of the art.

A virus vaccine composition of the present invention can comprise from about $10^2$–$10^9$ plaque forming units (PFU)/ml, or any range or value therein, where the virus is attenuated. A vaccine composition comprising an inactivated virus can comprise an amount of virus corresponding to about 0.1 to 200 μg of hemagglutinin protein/ml, or any range or value therein.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow, infra, Goodman, infra, Avery's, infra, Osol, infra and Katzung, infra, which are entirely incorporated herein by reference, included all references cited therein.

When a vaccine composition of the present invention is used for administration to an individual, it can further comprise salts, buffers, adjuvants, or other substances which are desirable for improving the efficacy of the composition. Adjuvants are substances that can be used to augment a specific immune response. Normally, the adjuvant and the composition are mixed prior to presentation to the immune system, or presented separately, but into the same site of the mammal being immunized. Examples of materials suitable for use in vaccine compositions are provided in Osol, A., ed., *Remington's Pharmaceutical Sciences*, Mack Publishing Co, Easton, Pa. (1980), pp. 1324–1341, which reference is entirely incorporated herein by reference.

Heterogeneity in the vaccine may be provided by mixing replicated influenza viruses for at least two mammalian influenza virus strains, such as 2–50 strains or any range or value therein. Influenza A or B virus strains having a modem antigenic composition are preferred. According to the present invention, vaccines can be provided for variations in a single strain of an influenza virus or for more than one strain of influenza viruses, using techniques known in the art.

A pharmaceutical composition according to the present invention may further or additionally comprise at least one viral chemotherapeutic compound, including, but not limited to, gamma globulin, amantadine, guanidine, hydroxybenzimidazole, interferon-α, interferon-β, interferon-γ, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir. See, e.g., Katzung, infra, and the references cited therein on pages 798–800 and 680–681, respectively, which references are herein entirely incorporated by reference.

The vaccine can also contain variable but small quantities of endotoxin, free formaldehyde, and preservative, which have been found safe and not contributing to the reactogenicity of the vaccines for humans.

Pharmaceutical Purposes

The administration of the vaccine composition (or the antisera that it elicits) may be for either a "prophylactic" or "therapeutic" purpose. When provided prophylactically, the compositions are provided before any symptom of influenza viral infection becomes manifest. The prophylactic administration of the composition serves to prevent or attenuate any subsequent infection. When provided therapeutically, the attenuated or inactivated viral vaccine is provided upon the detection of a symptom of actual infection. The therapeutic administration of the compound(s) serves to attenuate any actual infection. See, e.g., Berkow, infra, Goodman, infra, Avery, infra and Katzung, infra, which are entirely incorporated herein by reference, including all references cited therein.

An attenuated or inactivated vaccine composition of the present invention may thus be provided either before the onset of infection (so as to prevent or attenuate an anticipated infection) or after the initiation of an actual infection.

A composition is said to be "pharmacologically acceptable" if its administration can be tolerated by a recipient patient. Such an agent is said to be administered in a "therapeutically effective amount" if the amount administered is physiologically significant. A vaccine or composition of the present invention is physiologically significant if its presence results in a detectable change in the physiology of a recipient patient that enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the inlfuenza virus infection.

Pharmaceutical Administration

A vaccine of the present invention may confer resistance to one or more influenza strains by either passive immunization or active immunization. In active immunization, an inactivated or attenuated live vaccine composition is administered prophylactically, according to a method of the present invention. In another embodiment as passive immunization, the vaccine is provided to a host (i.e. a mammal), and the elicited antisera is recovered and administered to a recipient suspected of having an infection caused by at least one influenza virus strain.

In a second embodiment, the vaccine is provided to a mammalian female (at or prior to pregnancy or parturition), under conditions of time and amount sufficient to cause the production of antisera which serve to protect both the female and the fetus or newborn (via passive incorporation of the antibodies across the placenta or in the mother's milk).

The present invention thus includes methods for preventing or attenuating infection by at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purpose, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow, infra, Goodman, infra, Avery, infra and Katzung, infra, which are entirely incorporated herein by reference, including all references cited therein.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a vaccine composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow et al., eds., *The Merck Manual*, 16th edition, Merck and Co., Rahway, N.J., 1992; Goodman et al., eds., *Goodman and-Gilman's The Pharmacological*

Basis of Therapeutics, 8th edition, Pergamon Press, Inc., Elmsford, N.Y., (1990); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, Mass. (1985); and Katsung, infra, which references and references cited therein, are entirely incorporated herein by reference.

The dosage of an attenuated virus vaccine for a mammalian (e.g., human) adult can be from about $10^3$–$10^7$ plaque forming units (PFU)/kg, or any range or value therein. The dose of inactivated vaccine can range from about 1 to 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1–50 µg or any range or value therein, or the amount recommended by the U.S. Public Health Service (PHS), which is usually 15 µg, per component for older children $\geq 3$ years of age, and 7.5 µg per component for children <3 years of age. The quantity of NA can also be standardized, however this glycoprotein can be labile during the process of purification and storage (Kendal et al., *Infect. Immun.* 29:966–971 (1980); Kerr et al., *Lancet* 1:291–295 (1975)). Each 0.5-ml dose of vaccine preferably contains approximately 1–50 billion virus particles, and preferably 10 billion particles.

Having now generally described the invention, the same will be more readily understood through reference to the following examples provided by way of illustration, and are not intended to be limiting of the present invention.

EXAMPLE 1

Reduced Production of Influenza Virus in Vero Cell Cultures is due to Loss of Trypsin in the Culture Medium Material & Methods Cells. The Vero cell line (ATCC No. X38) (WHO-approved) was obtained from the American Type Culture Collection (ATCC) at the 134th passage. The cells were cultivated as monolayers in 250 cm³ flasks at 37° C. and 5% $CO_2$ in a growth medium of Eagles minimal essential medium (MEM) supplemented with 10% unheated fetal calf serum. For the growth of Madin-Darby canine kidney (MDCK) cells and rhesus monkey kidney (LLC-MK2) cells, the medium used was MEM with 5% fetal calf serum heated 30 minutes at 56° C. For the cultivation of a swine kidney cell line (SwK), RPMI 1640 medium was used with 5% heated fetal calf serum. For the experiments involving infection or mock-infection, the cells were grown either in 50 cm³ flasks or in 6 well, 24-well and 96-well plates (Falcon Labware). Cell monolayers were washed three times with PBS and overlaid with maintenance medium. The latter had the same composition as the growth medium for each cell line, the serum being omitted and 0.3% bovine serum albumin (BSA) added. Unless otherwise stated, the maintenance medium contained L-1-tosylamide-2-phenylethyl chloromethyl ketone (TPCK) trypsin (Worthington Diagnostics, Freehold, N.J.) at 1.0 µg/ml. Plaque assays were performed with TPCK trypsin (2.5 µg/ml).

Viruses. Vero-adapted influenza A/England/1/53 (H1N1) High Growth (HG), A/FW/1/50 (H1N1), and reassortant X-31 (H3N2) obtained from the parents A/Aichi/2/68 X (B3N2) PR/8/34 (H1N1) viruses were used. The viruses were passaged 5 times in Vero cell cultures, and the final stock virus preparations contained $10^{7.3}$ to $10^{8.25}$ $TCID_{50}$/0.2 ml and 32 to 128 HAU. In the preliminary experiments, the Vero-adapted A/Rome/49 (H1N1) strain was used ($10^{6.7}$ $TCID_{50}$/0.2 ml, 16 to 32 HAU). HA and infectivity titration were performed essentially as described in "Advanced Laboratory Techniques for Influenza Diagnosis" (*Immunol. Ser.* 6, pp. 51–57 (1975)). HA titrations were done in microtiter plates. Infectivity was measured by an end point titration technique in MDCK cells grown in 96-well plates with cytopathic effect (CPE) evaluation at 72 hours postinfection (Table 1).

Results: Restoration of Multicycle virus Growth by Repeated Addition of Trypsin. To verify that the abrogation of influenza virus accumulation in Vero cell cultures was due to the loss of trypsin activity in the culture medium, several experiments were performed in which trypsin concentration was restored during influenza infection in Vero cells by repeated additions of trypsin to the culture medium. This procedure led to an increase of the virus production in the cultures infected with low input doses, thus ensuring high final yields despite the low multiplicity of infection, as shown in Table 2. The effect on viral accumulation due to loss of trypsin activity was especially evident in 50 cm³ flasks (Table 2) and 6-well plates with dense confluent monolayers (Table 3), that is, in the conditions favoring a rapid loss of trypsin activity due to high numbers of Vero cells. In 6-well plates with nonconfluent monolayers, and in 24-well plates, the loss of trypsin activity and corresponding lower viral accumulation was much less dramatic because here the multicycle growth of the virus was supported under standard conditions (Table 3). Thus, since Vero cells are suggested to produce one or more factors that inactivate trypsin activity, this inactivation was reduced (and viral growth increased) by providing a relatively higher proportion of trypsin containing medium to Vero cells in the culture dishes or flasks.

EXAMPLE 2

Evaluation of Influenza A Virus Replication in Vero Cell Cultures

Materials & Methods

Viruses. To identify a suitable high growth strain, Vero cells were infected with the A/England/1/53 (H1N1) (HG) strain of influenza virus, a reassortant containing the gene segments coding for the two surface glycoproteins (HA and NA) from A/England/1/53 (H1N1) and the remaining six genes from A/PR/8/34 (H1N1). For the first four passages, the virus was left to adsorb for 1 hour at 37° C., after which the monolayer was washed twice with warm phosphate buffered saline (PBS) solution to remove the unabsorbed viruses. Serum-free MEM with 0.3% BSA was then added; the maintenance medium contained TPCK-treated trypsin at 1.0 µg/ml. The input dose of virus was $10$–$10^{-3}$ PFU/cell. The material for further passage was collected 72 hours postinfection (p.i.), with trypsin (final concentration, 1.0 µg/ml) added at 48 hours p.i. Cells were infected with serial 10-fold dilutions of viruses added to the washed cell monolayer without previous adsorption. Virus accumulation was estimated by visual determination of the CPE and HA titration of culture fluid at different times p.i. (24, 48 and 72 hours). Infectivity titrations were performed in 96-well plates. Tissue culture infectious doses ($TCID_{50}$/ml) and egg infectious doses ($EID_{50}$/ml) values were calculated by the formula of Karber (*Arch. Exp. Path. Pharmak.* 162:480–483 (1931)).

Virus-containing culture fluids were concentrated in an Amicon system and purified by differential sedimentation through 25–70% sucrose gradients. Whole virus protein estimates were made by the method of Bradford (1976). To determine the yield of HA protein in viruses grown in Vero and MDCK cells, the virus proteins were separated by gradient (4–10%) SDS-PAGE and intensity of Coomassie blue-stained protein bands was quantitated by densitometry.

Virus isolation from clinical material. Influenza A viruses were isolated from the throat washings of patients with clinical signs of influenza and collected in PBS to which 0.7% BSA was added. Cell cultures (both Vero and MDCK) or embryonated chicken eggs were infected directly with freshly collected (not frozen) throat washings. Chicken eggs were inoculated amniotically and allantoically. Clinical samples used for isolation were inoculated undiluted and at $10^{-1}$ and $10^{-2}$ dilutions and incubated for 72–96 hours. Trypsin was added at 0 and 48 hours p.i. (1.0 μg/ml) and virus yield tested for virus replication with chicken and guinea pig erythrocytes. Each sample was given at least two passages in chicken eggs or cell culture before being considered negative.

Immunological tests. Monoclonal antibodies to the A/Baylor/5700/82 (H1N1) and A/Baylor/11515/82 (H1N1) strains were prepared by the method of Köhler & Milstein, *Eur. J Immunol.* 6:511–519 (1976). Polyclonal antisera to influenza A/England/1/53 virus (20 passages in Vero cells) were prepared in chickens by intravenous injection of virus-containing culture fluid. HA and HI reactions were performed in microtiter plates with 0.5% (v/v) chicken erythrocytes. Guinea pig erythrocytes 0.5% (v/v) were used to test for the presence of primary influenza A isolates from the 1993–1994 winter epidemic season.

Gene amplification. RNA was isolated by treating allantoic or culture virus containing fluids with proteinase K and sodium dodecyl sulfate and then extracting the product with chloroform:phenol (1:1) and ethanol precipitation as previously described (Bean et al., (1980)). Viral RNA was converted to cDNA with the use of U12 (5'AGCGAAAGCAGG3')(SEQ ID NO:1) and AMV reverse transcriptase. The sequences of the oligonucleotide primers used in this study for molecular characterization of the internal genes (PB2, PB1, PA, NS and M) are readily available.

Amplification proceeded through a total of 35 cycles of denaturation at 95° C. (1 min), annealing at 50° C. (1 min.), and primer extension at 74° C. (3 min.). Amplified DNAs were analyzed by electrophoresis, visualized with ethidium bromide and then purified with either the Magic PCR Preps DNA purification system™ (Promega, Madison, Wis.) or the Geneclean R Kit™ (BIO 101, La Jolla, Calif.) according to the manufacturers' instructions.

Nucleotide sequence determination. Nucleotide sequencing was performed by the dideoxynucleotide chain termination method with the Fmol™ DNA sequencing system (Promega). The reaction products were separated on 6% polyacrylamide-7M urea gels, 0.4 mm thick.

Results

Screening of influenza A viruses in Vero cells. Influenza viruses can replicate to high titers in a limited number of cultured mammalian cells, provided that trypsin is present for cleavage of the HA molecule. To determine whether Vero cells were a suitable alternative system to chicken eggs for replication of influenza A viruses, a virus repository was screened for selection of a master strain that would replicate sufficiently in the mammalian epithelial-like cell line. MDCK cells, which are widely used to isolate and culture viruses, were included in the study as a reference.

The influenza A virus strains that were examined had been isolated from a wide range of human and avian hosts, and represented 12 of the 14 HA (not H5 and H7) and 9 NA subtypes. Viruses were passaged three times in Vero and MDCK cells with trypsin, and the virus yield was estimated from HA and infectivity titers. Of the 72 strains investigated, 65 (90.3%) replicated to the level that can be detected by HA titration in Vero cells after the first passage and 37 (51.4%) after the second. By comparison, all strains could replicate in MDCK cells during the first and second passages. Six human viruses were selected as the strains with the highest growth potential (Table 4), among which A/England/1/53 (H1N1) (HG) virus was chosen for further adaptation to Vero cells to optimize growth of virus in Vero cells.

If the A/England/1/53 (H1N1) (HG) virus is to be used as a master strain for generation of high growth reassortants, it is necessary to establish the genotype of this virus. Therefore, we partially sequenced the genes encoding the internal proteins and compared their nucleotide sequence with the prototype influenza strain, A/PR/8/34 (H1N1). As shown in Table 5, the A/England/1/53 (HG) strain selected for adaptation to growth in Vero cells is itself a reassortant between the original A/England/1/53 strain and A/PR/8/34. Six genes of the reassortant encoded internal proteins of A/PR/8/34 and two surface glycoproteins of A/England/1/53.

Infectivity of A/England/1/53 (HG) after serial passaging. To enhance the yield of virus in Vero cells, we performed 20 serial passages of A/England/1/53 (H1N1) (HG) at limiting dilutions, comparing the results with those for the parental strain (Table 6). Although the infectivity of the parent was lower in Vero cells than in either MDCK or chicken embryos, the progeny showed increased activity in Vero cells by the tenth passage, exceeding that in both reference systems. By the twentieth passage, the infectivity of the virus was superior in Vero cells in the continuous presence of trypsin, but the HA titers remained comparable (64–128).

The infectivity titer ($TCID_{50}$) was 26 times higher (6.95 vs 8.37) than that of the parental strain. By contrast, adaptation of replication in Vero cells resulted in a slight attenuation of the virus when grown in chicken embryos, as indicated by a reproducible decrease in $EID_{50}$ titer from 8.2 to 7.7 $\log_{10}$. The plaques formed by the Vero-adapted A/England/1/53 (HG) influenza strain were not as clear in Vero as in MDCK cells, and the efficiency of production was 10-fold lower. Plaque-forming capacity in Vero cells increased during serial passages of the virus but not in direct relation to the $TCID_{50}$ titers. Thus, after 20 serial passages in Vero cells in the continuous presence of trypsin, the yield of infectious virus was high by comparison with that in MDCK cells and embryonated chicken eggs.

Viral protein yield of influenza A/England/1/53 (HG) in Vero and MDCK cells. Viral protein yield is an important feature of any system used to produce influenza virus vaccines. To establish the amount of virus-specific proteins that can be obtained from Vero cells, we compared the protein yields of A/England/1/53 (HG) (20-passage) virus after replication in Vero and MDCK cells (Table 7). Determination of the HA protein yield was done using SDS-PAGE separated virus proteins and was quantitated by densitometry. Tests of culture fluids indicated that approximately $6 \times 10^8$ of infected cells could produce 4.38 mg of virus protein in Vero and 4.13 mg in MDCK cells. It was also possible to obtain viral proteins from disrupted, virus-infected cells of either type; the protein yields were lower than in the supernatant but there was no significant difference between the cell types in amount of virus protein.

Antigenic stability of the Vero-adapted influenza A/England/1/53 (HG) virus. Because repeated passage of influenza viruses in mammalian cells could lead to changes in antigenicity, it was thought that it was important to assess the influenza virus adapted to Vero cell culture for this property. In HI tests with both polyclonal (chicken, rabbit and goat) antisera to cross reacting influenza A (H1N1) viruses and with anti-HA monoclonal antibodies, there were no appreciable differences in HA reactivity between the parental strain of A/England/1/53 (HG) and its serially passaged variants (Table 8). This finding, which extends to antibodies specific for H1N1 strains other than A/England/1/53 (HG), indicates that serial passage of the virus in Vero cells did not modify its HA antigenic properties.

Primary isolation of influenza A viruses. Currently, MDCK cells provide the most sensitive host cell system for the primary clinical isolation of influenza viruses directly from patients. Vero cells have been successfully used to isolate parainfluenza and mumps viruses, but they were judged unsuitable for the isolation of influenza viruses. To reassess this issue, we tested nine clinical specimens collected during the 1993–1994 epidemic season in three culture systems (Vero and MDCK cells and embryonated chicken eggs). Six influenza A (H3N2) strains were isolated in Vero cells, seven in MDCK cells and only two in embryonated chicken eggs (Table 9). Two samples failed to yield virus in any host system. During the first passage in Vero cells, CPE (observed 48–72 hours after inoculation) was the only evidence of virus reproduction. HA activity was detectable on the 2nd passage, and by the 3rd passage the positive samples produced both CPEs and HA titers that ranged from 2–32. In all three culture systems, it was necessary to use guinea pig erythrocytes to determine HA titers. Chicken erythrocytes failed to be agglutinated according to known methods. To examine whether replication of influenza A (H3N2) viruses in Vero cells could select antigenic variants, we analyzed viruses that had been passaged three times in this system. The reactivity patterns of the HA with polyclonal antisera to reference A (H3N2) influenza strains and monoclonal anti-HA antibodies did not indicate differences between the strains isolated in Vero cells. These results indicate that Vero cells would provide a useful and nearly as sensitive a culture system as MDCK cells for primary isolation of influenza A (H3N2) viruses, provided that trypsin was present continuously in the Vero cell cultures.

EXAMPLE 3

Production of Influenza B Virus in Vero Cell Cultures

Materials and Methods

Cells. The Vero cell line was obtained from the American Type Culture Collection (ATCC, Rockville, Md.) at the 136th passage. Cells were cultivated as a monolayer at 37° C. and 5% $CO_2$ in Eagle's minimal essential medium (MEM) containing 10% unheated fetal calf serum (FCS), MDCK cells (London, Mill Hill) obtained at a low-passage level, were grown in MEM with 5% heat-inactivated FCS. Plaque assays were performed with TPCK-treated trypsin (2.5μg/ml; Worthington Diagnostics Freehold, N.J.) as described earlier (Hayden, F. G. et al., *Antimicrob. Agents Chemother.* 17:865–870 (1980)). Plaques were counted on the third day after infection.

Virus replication. The replicative properties of egg-grown influenza A and B viruses, obtained from the repository at St. Jude Children's Research Hospital, were determined in Vero cells. The cells were infected with serial 10-fold dilutions ($10^1 \rightarrow 10^3$) of virus in serum-free MEM with 0.3% BSA, which was added to the washed monolayer without previous incubation; the maintenance medium contained 1.0 μg/ml of TPCK-treated trypsin added at 0,24 and 48 hr. postinfection. Virus yield was determined by HA and PFU titration of culture medium after incubation for 72 or 96 hr. at 33° C. $TCID_{50}$/ml and $EID_{50}$/ml values were calculated as described by Karber, G., *Arch. Exp. Path. Phannak*, 162:480–483 (1931).

Primary isolation. Vero and MDCK cells were infected with the throat cultures of patients with clinical signs of influenza. Only samples that were positive for influenza virus by indirect immunofluorescence test or by previous isolation in eggs or MDCK cells were used. Infected cells were incubated for 72–96 hr. postinfection at 33° C. (for influenza B viruses) or 37° C. (for influenza A viruses); trypsin was added at 0,24 and 48 hr. postinfection (1.0μg/ml).

Adaptation to growth in the Vero cells. Adaptation to growth in Vero cells was performed for the A/England/1/53 (H1N1) (HG) and B/Ann Arbor/1/86 strains by 20 serial passages at limiting dilutions as previously described (Govorkova, E. A. et al., *J. Infect. Dis.* 172:250–253 (1995)) and as described infra.

Antigenic analysis. Monoclonal antibodies to the HA of egg-grown A/Baylor/11515/82 (H1N1), A/Baylor/5700/82 (H1N1), B/Ann Arbor/1/86, B/Memphis/6/86 and MDCK-grown B/Memphis/6/86 viruses were prepared according to Köhler & Milstein, (*Eur. J Immunol.* 6:511–519 (1976)). Monoclonal anti-HA and polyclonal antibodies were used for antigenic characterization of the influenza A and B viruses in a hemagglutinin-inhibition (HI) reaction with 0.5% (v/v) chicken erythrocytes.

Analysis of the abundance of SA α2,3 Gal and SA α2,6 Gal linkages on Vero and MDCK cells. This study was performed with the digoxigenin glycan differentiation kit (Boehringer Mannheim Biochemica; Germany). Briefly, Vero or MDCK cells were washed twice in PBS containing 10 mM glycine, then once with buffer 1 (50 mM Tris-HCI; 0.15M NaCl; 1 mM $MgCl_2$; 1 mM $MnCl_2$; 1 mM $CaCl_2$; pH=7.5). Digoxigenin (DIG)-labeled lectins, *Sambus nigra* agglutinin (SNA) specific for SA α2,6 Gal, and *Maackia amurensis* agglutinin (MAA) specific for SA α2,3 Gal, were dissolved in buffer 1 and then incubated with the cells for 1 hr. at room temperature. After three washes, the cells were incubated with anti-DIG-fluoresceinated, Fab fragments (1:40 diluted in buffer 1) for 1 hr. at room temperature. After three washes, the cells were analyzed for relative fluorescence intensity on a FACScan fluorospectrometer (Becton Dickinson).

Surface immunofluorescence. Vero or MDCK cells were infected with A/England/1/53 (H1N1) or B/Ann Arbor/1/86 at different m.o.i.'s (0.1, 1.0 and 10.0 PFU/cell). Cell suspensions were fixed at 6 hr. postinfection with 4% paraformaldehyde in PBS at room temperature for 20 min. For detection of the HA of influenza viruses, we used a panel of monoclonal antibodies to the HA's of A/Baylor/5700/82 (H1N1) and B/Memphis/6/86. The cells were incubated with 1:100 dilution of monoclonal antibodies in PBS with 0.2% gelatin, 0.05% Tween 20 and 10.0% normal goat antisera for 1 hr. at room temperature. After three extensive washes with PBS-0.05% Tween 20, the cells were incubated with fluorescein-conjugated goat anti-mouse antibodies (Sigma; 1:100 dilution) for 1 hr. at room temperature. After three washes with PBS-0.05% Tween 20, the cells were analyzed on a FACScan fluorospectrometer.

Protein gel electrophoresis and radioimmunoprecipitation. Vero or MDCK cells were infected with either A/England/1/53 (H1N1) or B/Ann Arbor/1/86 at an m.o.i. ~30 PFU/cell. After adsorption for 1 hr. at 37° C. in virus growth medium, the cells were washed and incubated for 5 hr. (influenza A strain) or 8 hr. (influenza B strain) in the labeling medium (DMEM without methionine and cystine; ICN Biomedicals, Inc., Costa Mesa, Calif.). Viral proteins were radioactively labeled with Tran ($^{35}$S) methionine/cysteine (ICN chemicals; 100 $\mu$Ci/ml) for 2 hr. at 37° C. Viral proteins—HA, nucleoprotein (NP), and matrix (M1 and M2) were analyzed by radioimmunoprecipitation with specific monoclonal antibodies. The cell lysate (100 $\mu$l) was treated with 1–2 $\mu$l of specific virus antibody and incubated for 2 hr. at room temperature with constant inverting. These experiments relied on monoclonal antibodies to HA of A/Baylor/5700/82 (H1N1) virus, to NP of A/WSN/33 (H1N1) and to HA of B/Memphis/6/86. Monoclonal antibodies to the M2 protein (14 C2) were generously provided by Dr. R. A. Lamb (Department of Biochemistry, Molecular and Cell Biology, Northwestern University, Evanston, Ill.). A rabbit anti-mouse protein A suspension of beads was added to the supernatant, which then was incubated further for 2 hr. at room temperature. The immunocomplexes were pelleted and washed three times with RIPA buffer (50 mM Tris-HCI, pH 7.6; 150 mM NaCl, 0.05 v/v Triton X-100, 1.0% sodium deoxycholate, 1.0% SDS, 1 mM EDTA), heated at 100° C. for 5 min in 2× Laemmli loading buffer and analyzed by 15% SDS polyacrylamide gel electrophoresis (PAGE) according to the method of Laemmli, U. K., *Nature* 227:680–685 (1970). Imaging and quantitation were performed with a Molecular Dynamics phosphorimager and Image Quant Software™, respectively.

Gene amplification. RNA extraction, cDNA preparation and the polymerase chain reactions (PCR) were performed as previously described (Gubareva, L. V. et al., *Virology* 199:89–97 (1994)).

Nucleotide sequence determination. Nucleotide sequencing was performed by the dideoxynucleotide chain termination method (Sanger, F. et al., *Proc. Natl. Acad. Sci. USA* 74:5463–5467 (1977)) with the FMOL™ DNA sequencing system (Promega) and end-labeled primers.

Electron microscopy. Vero and MDCK cell monolayers were infected with Vero-adapted influenza strains (A/England/1/53 (H1N1) and B/Ann Arbor/1/86) at an m.o.i. of 0.001 PFU/cell. Infected and control cell monolayers were fixed at 48 hr. postinfection in cacodylate-buffered 2.5% glutaraldehyde, postfixed in 1% osmium tetroxide, dehydrated in graded series of alcohols and embedded in Spurr low-viscosity embedding medium (Ladd Research Industries, Burlington, Vt.). Ultrathin sections of cells were cut with a diamond knife on a Sorvall MT 6000 ultramicrotome, and the sections were examined in a Phillips EM 301 electron microscope operated at 80 kV.

Immunohistochemical assay. To detect apoptotic changes in virus-infected Vero and MDCK cells, we used a commercial kit (Apoptag™; Oncor, Gaithersburg, Md.) according to the manufacturer's instructions.

Thus, the Vero cell line appears to offer useful system for primary isolation of influenza A and B viruses and could support virus multiplication to high infectivity titers.

Results

Primary Isolation and replication of influenza A and B viruses in Vero cells. High rates of primary isolation of influenza A virus from clinical specimens (n=27) were obtained with Vero and MDCK cells but not with eggs: 70.4%, 74.1% and 14.8%, respectively (Table 10). By contrast, the percentage of specimens (n=21) yielding influenza B virus was comparable in Vero cells (47.6%) and eggs (42.9%) but higher in MDCK cells (57.1%). Ranges of $TCID_{50}$ titers were essentially the same whether viruses were grown in Vero or MDCK cells or eggs (Table 10).

Antigenic and genetic stability of the HA of influenza strains isolated and grown in different host cell systems. To determine whether replication of influenza viruses in Vero cell line selects host cell-mediated HA variants, we performed antigenic and sequence analyses of the HA molecule. HI testing with polyclonal and anti-HA monoclonal antibodies revealed that the egg-grown B/Ann Arbor/1/86 strain was antigenically stable in Vero cells, as it retained its original antigenic characteristics during 20 passages in the mammalian host-cell system (Table 11).

It was also important to determine if growth in Vero cells selected variant virus populations during primary isolation. We therefore compared the HA sequence of influenza B viruses (B/Memphis/1/93) isolated in Vero or MDCK cells or chicken eggs. The results indicated amino acid substitutions in virus grown and isolated in chicken eggs, in contrast to findings in Vero- and MDCK-grown viruses (Table 12). This change involved residues 196 (Asp→Asn) and 198 (Ala→Thr) at the head of the HA molecule. The HA1 region of influenza B/Memphis/1/93 virus isolated and passaged in Vero cells was indistinguishable from that in the MDCK-grown counterpart.

Thus, the similarity of antigenic and molecular characteristics of influenza A and B viruses grown in Vero cells to MDCK grown virus suggests that this host system would generate virus populations analogous to those found in naturally infected hosts.

Receptor specificity of Vero cells and efficiency of influenza virus A and B infection. Human influenza viruses bind preferentially to SA α2,6 Gal linkages and viruses from lower mammals to SA α2,3 Gal (Baum & Paulson, *Acta Histochem. Suppl.* 40:35–38 (1990)). To characterize the nature and distribution of influenza virus-binding receptors on the surface of Vero cells, we used indirect immunofluorescence microscopy with different lectins specific for either N-acetylneuraminic acid α2,3 galactose (NeuAc α2,3 Gal) or N-acetylneuraminic acid α2,6 galactose (NeuAc α2,6 Gal).

The Maackia amurensis agglutinin (MAA), which is specific for NeuAc α2,3 Gal, binds strongly to the surface of Vero cells, whereas the *Sambucus niigra* lectin (SNA), which recognizes NeuAc α2,6 Gal, binds only weakly to the surface of Vero cells. Both types of lectins bind strongly to MDCK cells. In these experiments, FACS analysis revealed that the receptor specificity on Vero cells was predominantly NeuAc α2,3 Gal (~90.0%), with a minority of cells also possessing the NeuAc α2,6 Gal linkage (~21.0%). This result contrasts with the nearly equal proportions of these linkages found on more than 85% of the MDCK cells examined (FIG. 1). Thus, the Vero cell population probably comprises two distinct groups of receptor-bearing cells, one containing both types of sialyloligosaccharides specific for influenza viruses and the other primarily NeuAc α2,3 Gal.

Conceivably, the limited availability of NeuAc α2,6 Gal linkages on Vero cells could affect the efficiency of infection by influenza A and B viruses. We tested this prediction by determining the percentage of cells expressing the HA molecule at different m.o.i.'s at 6 hr. postinfection (Table 13). The results of FACS analysis showed similar efficiencies of infection between Vero and MDCK cells infected with either influenza A or B viruses. At an m.o.i. of 10.0 PFU/cell, 87% of Vero and 91% of MDCK cells were infected with the influenza A/England/1/53 strain. Slightly smaller percentages of cells expressing the HA were infected by the influenza B/Ann Arbor/1/86 virus: 81% for Vero and 85% for MDCK (Table 13). Similar correlations were observed between Vero and MDCK cells at m.o.i.'s of 0.1 and 1.0 PFU/cell.

These results indicate that although human influenza viruses have a preference for α2,6 Gal-linked sialic acid, they are still able to infect and replicate efficiently in Vero cells, where the primary linkage is NeuAc α2,3 Gal as long as trypsin is continuously present in the culture medium.

Protein synthesis in Vero and MDCK cells infected with influenza A and B viruses. We also thought it important to assess the pattern of protein synthesis of influenza viruses grown in Vero versus MDCK cells. Here we analyzed the protein synthesis in Vero cells infected with either influenza A/England/1/53 or B/Ann Arbor/1/86 as compared to infection in MDCK cells. The protein patterns of A/England/1/53 infected Vero cells demonstrated that most virus specific polypeptides are synthesized in proportions similar to those in MDCK cells (FIG. 2A). There were no differences in electrophoretic migration of viral proteins synthesized in both cell lines infected with parental or Vero-adapted influenza A/England/1/53 strain (results not shown). Under the conditions of these experiments, M1 and NS1 migrated close to each other, so that additional resolution of immunoprecipitates obtained with mouse anti-M1 monoclonal antibodies was attempted using SDS-PAGE (FIG. 2A).

Figure 2B:
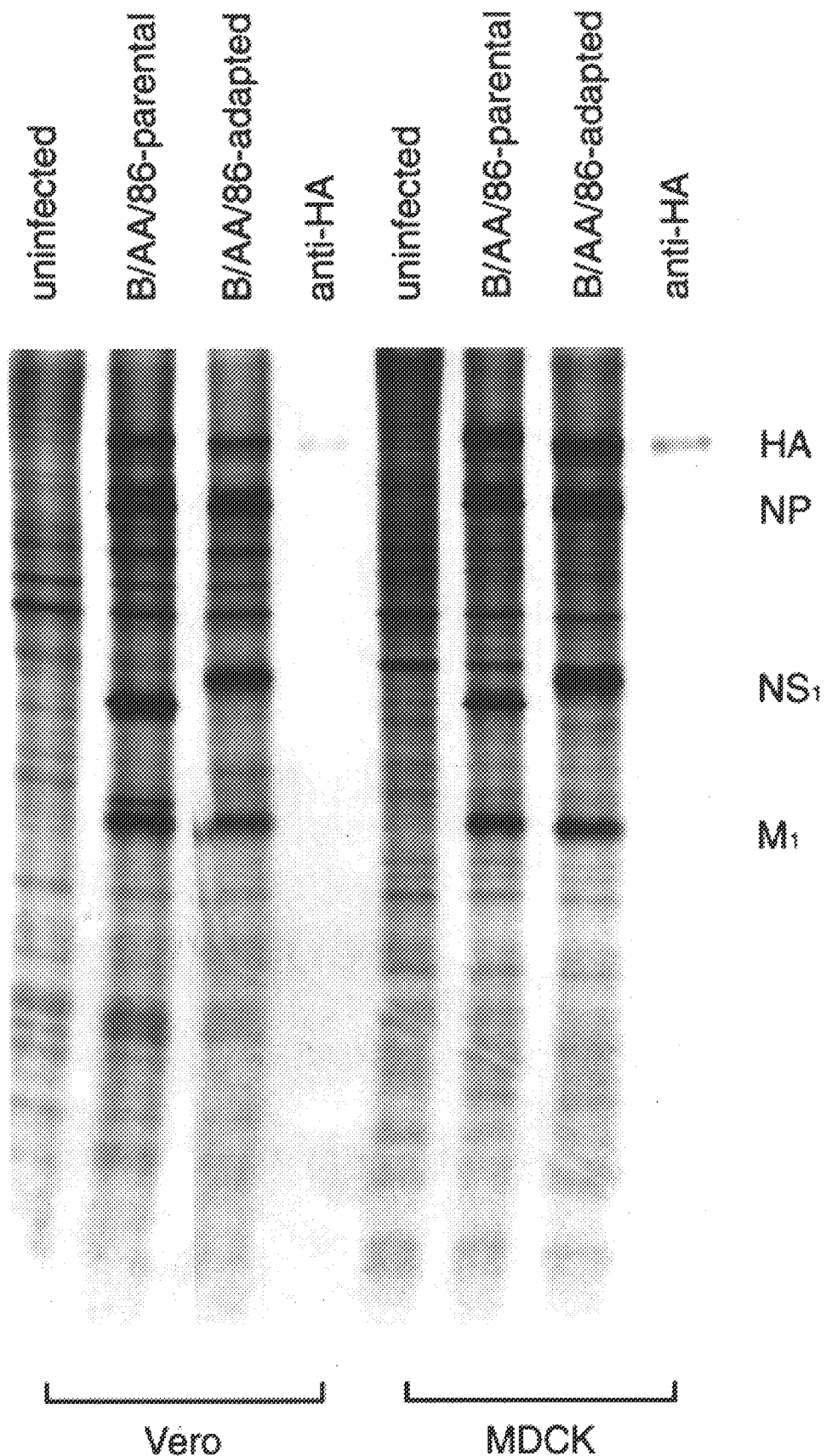

Relative amounts of viral proteins synthesized in MDCK and Vero cells infected with influenza A virus are reported in Table 14. After 5 hr. postinfection, the two cell types contained similar proportions of NP, M2 and NS2, while approximately 10% more HA and 10% less M1/NSI were detected in Vero compared to MDCK cells. To determine which protein (M1 or NS1) was under-produced in Vero cells, we also analyzed the material immunoprecipitated from infected cells with anti-M1 monoclonal antibodies. The results (not shown) demonstrated a slightly lower amount of M1 protein in Vero cells (9.2% vs 14.7% in MDCK cells). As shown in FIG. 2B and also Table 14, the pattern of protein synthesis and proportions of the HA, NP, M1 and NS1 proteins were similar in Vero and MDCK cells infected with influenza B/Ann Arbor/1/86 strain.

Figure 3E:
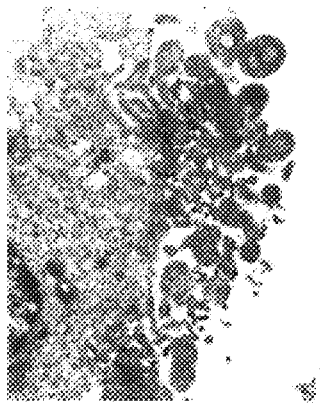
FIGS. 3A–F. Electron micrographs showing influenza A/England/1/53 (H1N1) virus infected Vero and MDCK cells. The virions that budded from the apical surface are shown for MDCK cells (FIG. 3A) and Vero cells (FIG. 3B). The nuclear breakdown (FIG. 3C, FIG. 3D) and cytoplasmic blebbing (FIG. 3E, FIG. 3F) typical of apoptotic cells is also observed with MDCK cells (FIG. 3C, FIG. 3E) and Vero cells (FIG. 3D, FIG. 3F). "v", virions; "b", blebbing of nuclear envelope. Magnification is ×9,250.
Figure 3C:
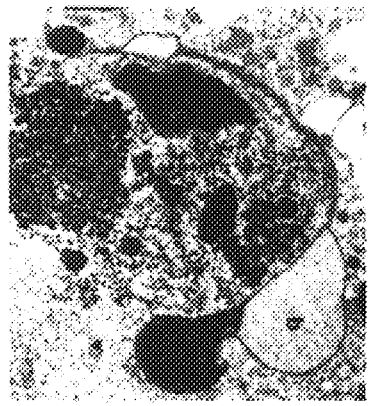
Figure 3A:
Figure 3F:
Figure 3D:
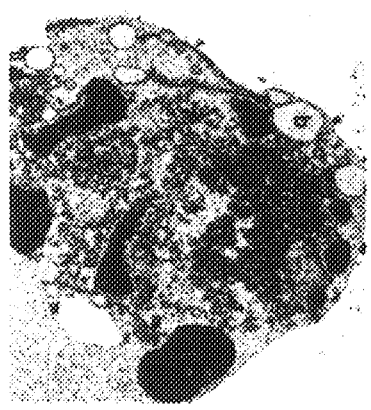
Figure 3B:

Ultrastructural features of virus-infected Vero cells. To determine if influenza virus-infected Vero cells show the same morphological changes as other polarized epithelial cells, we studied the ultrastructural features of these cells in comparison to MDCK cells, after infection with the A/England/1/53 and B/Ann Arbor/1/86 Vero-adapted influenza strains. At an m.o.i. of 0.001 PFU/cell, both types of cells showed nuclear and cytoplasmic inclusions typical of influenza virus-infected cells, as well as numerous budding virions (FIGS. 3A–B). As in MDCK cells, influenza A and B virions were released from the apical surface of Vero cells, a feature typical of epithelial cells infected with influenza virus. The budding virions in both Vero and MDCK cells appeared to be mainly filamentous. A portion of influenza A-and B-infected cells in both systems showed cytopathological changes indicative of apoptosis (FIGS. 3C–F, also Wyllie, A. H. et al., *Inter. Rev. Cytol.* 68:251–306 (1980)). The nuclear changes consisted of blebbing of the nuclear envelope and condensation of the chromatin. The cytoplasmic changes consisted of extensive vacuolation, blebbing and vesiculation of the plasma membrane to form "apoptotic bodies."

To confirm that our electron microscopic observations were indeed consistent with cell apoptotic changes, we examined infected Vero and MDCK cells with an assay that detects fragmented DNA in the cells. The results were positive for 20% to 30% of the infected cells, contrasted with none of the uninfected cells (not shown). This range of positivity may be underestimated, as many positive cells could have detached from the substratum during the extensive washing required by these procedures. In certain cells, the fluorescent label was clearly seen over spherical masses within the nucleus, which may represent condensed masses of degraded DNA. Thus, a substantial portion of infected Vero and MDCK cells undergo endonucleolytic cleavage of DNA—a feature typically seen in other types of cells infected with influenza virus (Takizawa, T. et al., *J. Gen. Virol.* 74:2347–2355 (1993); Hinshaw, V. S. et al., *J. Virol.* 68:3667–3673 (1994)).

Discussion. Several lines of evidence from the present study support the use of Vero cells as a host system for cultivation of influenza A and B viruses for vaccine production when trypsin is continuously present in the culture system: (I) efficiency of primary virus isolation and replication to high infectivity titers, (ii) genetic stability of the HA molecule with maintenance of antigenic properties characteristic of viruses derived from humans, (iii) similarities in the pattern of protein synthesis and morphological changes between virus-infected Vero and MDCK cells. Previous attempts to grow influenza virus in Vero cells were met with limited success (Demidova, S. A. et al., Vopr. *Virosol* (*Russian*) 346–352 (1979); Nakamura & Homma, *J Gen. Virol.* 56:199–202 (1981); Valette, M. et al., *Antimicrob. Agents Chemother.* 37:2239–2240 (1993)). Moreover, when Vero cells were infected with A/fowl plague/Rostock/34 (FPV, H7N1), very little infectious virus was released, and its spread was greatly impeded (Lau & Scholtissek, *Virology* 212:225–231 (1995)). It is now known that Vero cells rapidly destroy exogenous trypsin (Kaverin & Webster, *J. Virol.* 69:2700–2703 (1995)), limiting the replication of infectious viruses to a single cycle. It is now discovered that the stepwise addition of trypsin can circumvent the problem of trypsin inactivation or viral replication inhibition and ensure multicycle replication comparable in all respects to that seen with both human influenza A and B viruses grown in MDCK cells.

We also show that the HA1 region of influenza B viruses isolated and passaged in Vero cells is indistinguishable from that of MDCK-grown counterparts, supporting the conclusion that Vero cells do not select host cell-mediated HA variants. Similar correlations were reported by Katz & Webster, *J. Gen. Virol.* 73:1159–1165 (1992) for the HAs of influenza A (H3N2) viruses isolated in LLC-MK2 and primary guinea pig kidney cells and those of MDCK cell-grown viruses isolated from the same patient. The absence of host cell-specific modifications of the HA during primary isolation and subsequent passage in Vero cells is a critical requirement in validation of this cultivation system for the production of human influenza vaccines and diagnostic reagents. Amino acid substitution at positions 196–198, near the tip of the HA molecule, is known to be involved in host cell-mediated mutations (Robertson, J. S. et al., *Virology* 143:166–174 (1985); Robertson, J. S. et al., *Virology* 179:3540 (1990)). Further, the loss of a potential glycosylation site by egg-grown viruses was associated with alterations in binding of mono- and polyclonal antibodies to the HA molecule (Oxford, J. S. et al., *J. Gen. Virol.* 72:185–189 (1991)) and with attenuation of virulence for volunteers (Oxford, J. S. et al., *Arch. Virol.* 110:37 –46 (1990); Zuckerman, M. A. et al., *J. Infect. Dis.* 28:41–48 (1994)). Thus, the antigenic and nucleotide sequence similarities between the HAs of Vero- and MDCK-grown influenza B viruses provide reassurance against the generation of undesirable variants.

Receptor specificity is an important mechanism governing the susceptibility of cells to virus infection. In the absence of sialic acid receptors of the proper specificity, viruses may be unable to bind to the cell surface, thus eliminating the opportunity for productive infection. Although Vero cells bore a relatively low level of the NeuAc α2,6 Gal linkage, by comparison to MDCK cells, this deficiency did not appear to affect their susceptibility to either influenza A or B virus (Table 13). This finding raises the possibility that linkages other than NeuAc α2,3 Gal and NeuAc α2,6 Gal may be involved in the attachment of influenza viruses to host cells.

Effective virus replication depends on specific cellular requirements, including the synthesis, transport and processing of viral proteins needed to produce infectious virus. Although, in the present study, the amounts of HA and M1/NS1 synthesized by Vero and MDCK cells differed by an estimated 10%, this discrepancy did not affect the virus yield. This observation is consistent with data reported by Nakamura et al., *J. Gen. Virol.* 56:199–202 (1981) showing that the synthesis of M protein is selectively inhibited in Vero cells infected with influenza B/Lee/40 virus. By contrast, overproduction of M2 and NS2 proteins in Vero cells infected with A/FPV (H7N1) was recently described by Lau & Scholtissek, *Virology* 212:225–231 (1995). In any event, the amount of M1 produced in Vero cells seems to be sufficient to facilitate the nucleocytoplasmic transport of the nucleocapsid and the production of infectious virus.

Ultrastructural examination of influenza virus-infected Vero cells revealed morphological changes similar to those observed in MDCK cells. It is interesting that both cell lines produce predominantly filamentous viruses, which may explain the detection of lower HA levels than might be expected from the high infectivity rates associated with these host cell systems. Although influenza virus can induce apoptosis in other cell lines (Takizawa, T. et al., *J. Gen. Virol.* 74:2347–2355 (1993); Hinshaw, V. S. et al., *J. Virol.* 68:3667–3673 (1994)) the observations reported here provide the first morphological and cytochemical evidence of this effect in Vero cells.

The MDCK cell line has been widely touted as the optimal mammalian cell system for the isolation and growth of influenza viruses, but it has not yet been approved for use in vaccine production. A report that MDCK cells can induce tumors in nude mice raises questions about the suitability of this system for the production of live influenza virus vaccines. Thus, the Vero cell line grown in the continuous presence of trypsin offers an attractive alternative for the cultivation of influenza A and B viruses. This system is already in use for the production of other human virus vaccines and could readily be adapted to influenza viruses.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

TABLE 1

Accumulation of Influenza A/Rome/49 (H1N1) virus in MDCK cells and in Vero cells with trypsin in different plasticware

| | | Input dose ($TCID_{50}$ per flask or per well) | | | | | | |
|---|---|---|---|---|---|---|---|---|
| | | 10,000 | | 1,000 | | 100 | | 10 | |
| Cells | Plasticware / h.p.i.[1] | 48 | 72 | 48 | 72 | 48 | 72 | 48 | 72 |
| MDCK | 50 cm³ flasks | 32[2] | 128 | 64 | 128 | 32 | 128 | 16 | 128 |
| Vero | 50 cm³ flasks | 16 | 32 | 2 | 8 | 1 | 1 | 0 | 0 |
| Vero | 96-well plates | ND | 16 | ND | 16 | ND | 32 | ND | 32 |

[1] Hours post-infection (h.p.i.)
[2] Reciprocals of HA titer in culture fluid
ND = not done

TABLE 2

Effect of the restoration of trypsin concentration on X-31 virus grown in Vero cells in 50 cm³ flasks

| Inputdose($TCID_{50}$/flask) | $1.5 \times 10^5$ | | $1.5 \times 10^3$ | | $1.5 \times 10$ | |
|---|---|---|---|---|---|---|
| h.p.i.[1] | 48 | 72 | 48 | 72 | 48 | 72 |
| Trypsin added at 0 h.p.i. | 8[2] | 8 | 1 | 1 | 0 | 0 |
| Trypsin added at 0, 12, 24, and 48 h.p.i. | 64 | 128 | 32 | 128 | 4 | 128 |

[1] Hours post-infection
[2] Reciprocals of HA titers
TPCK - trypsin added to final concentration of 1.0 g/ml

TABLE 3

Effect of multiple trypsin addition on the growth of influenza A viruses in Vero cells in plates

| Exp. No. | Virus | Plates | State of the monolayer | Trypsin added at: | Input dose: (TCID$_{50}$ per well) | | | | | | | |
|---|---|---|---|---|---|---|---|---|---|---|---|---|
| | | | | | $10^4$ | | $10^3$ | | $10^2$ | | $10^1$ | |
| | | | | | 48 | 72 | 48 | 72 | 48 | 72 | 48 | 72 |
| 1 | FW/50 | 6-well | Dense | 0 h.p.i.[1] | 64 | 64 | 32 | 64 | 2 | 2 | 1 | 1 |
| | FW/50 | 6-well | Dense | 0, 24, 48 h.p.i. | 64 | 64 | 32 | 64 | 16 | 32 | 8 | 32 |
| | X-31 | 6-well | Dense | 0. h.p.i. | 64 | 64 | 16 | 16 | 1 | 2 | 0 | 1 |
| | X-31 | 6-well | Dense | 0, 24, 48 h.p.i. | 32 | 64 | 32 | 64 | 16 | 64 | 4 | 32 |
| 2 | FW/50 | 6-well | Non-confluent | 0. h.p.i. | 16 | 16 | 16 | 32 | 16 | 64 | 4 | 8 |
| | FW/50 | 6-well | Non-confluent | 0, 24, 48 h.p.i. | 16 | 16 | 16 | 32 | 16 | 64 | 4 | 32 |
| 3 | FW/50 | 24-well | Non-confluent | 0. h.p.i. | 32 | 32 | 32 | 32 | 16 | 64 | 4 | 32 |
| | FW/50 | 24-well | Non-confluent | 0, 24, 48 h.p.i. | 32 | 32 | 32 | 32 | 16 | 32 | 8 | 32 |
| | X-31 | 24-well | Non-confluent | 0. h.p.i. | 64 | 64 | 32 | 64 | 16 | 64 | 4 | 32 |
| | X-31 | 24-well | Non-confluent | 0, 24, 48 h.p.i. | 64 | 64 | 32 | 64 | 16 | 64 | 8 | 64 |

[1]Hours post-infection
[2]Reciprocals of HA titer in culture fluid

TABLE 4

Highest Yields of Influenza A Viruses in Vero Cells

| Virus | Subtype | Virus | HA Titer[1] | Infectivity titer[1] ($\log_{10}$ TCID$_{50}$/ml) |
|---|---|---|---|---|
| Human viruses | H1N1 | A/Bellamy/42 | 32 | 7.9 |
| | | A/Rome/49 | 64 | 7.7 |
| | | A/FW/1/50 | 64 | 7.6 |
| | | A/England/1/53 (HG) | 64 | 7.5 |
| | H2N2 | A/Japan/305/57 | 32 | 7.7 |
| | | A/Netherlands/65/63 | 64 | 7.6 |

[1]Titers were determined for the first passage and measured at 72 hours postinoculation.
HG = High Growth

TABLE 5

Genotyping of A/England/1/53 (H1N1) Influenza Virus

| | Genes and nucleotides analyzed | | | | | | | |
|---|---|---|---|---|---|---|---|---|
| Virus | PB2 969–1156 1480–1580 | PB1 360–535 1352–1487 | PA 20–227 478–606 | NP 1064–1246 | M 506–881 | NS 30–205 | HA | NA |
| A/PR/8 34 | P | P | P | P | P | P | P | P |
| A/Eng/1/53 (original) | E | E | E | E | E | E | E | E |
| A/Eng/1/53 (HG) | P | P | P | P | P | P | E | E |

P = genes from A/PR/8/32; E = genes from original A/England/153; HG = High Growth The origin of HA and NA was determined by HI and NI tests.

TABLE 6

Growth Characteristics of Influenza A/England/1/53 (H1N1) (HG) Virus After 10 and 20 Passages in Vero Cells

| | | Infectivity Titer[1] ($\log_{10}$) | | | Plaque-Forming Units[1] | |
|---|---|---|---|---|---|---|
| | | TCID$_{50}$/ml | | | ($\log_{10}$PFU/ml) | |
| Virus | HA Titer | MDCK | Vero | EID$_{50}$/ml | MDCK | Vero |
| A/Eng/1/53 (HG) parent (1P) | 64 | 7.70 | 6.95 | 8.20 | 8.70 | 7.18 |
| A/Eng/1/53 (HG) (10P) | 64 | 7.20 | 7.95 | 7.70 | 8.57 | 7.76 |
| A/Eng/1/53 (HG) (20P) | 64–128 | 7.57 | 8.37 | 7.70 | 8.65 | 7.70 |

TABLE 6-continued

Growth Characteristics of Influenza A/England/1/53 (H1N1) (HG) Virus After 10 and 20 Passages in Vero Cells

| Virus | HA Titer | Infectivity Titer[1] ($\log_{10}$) TCID$_{50}$/ml MDCK | Vero | EID$_{50}$/ml | Plaque-Forming Units[1] ($\log_{10}$PFU/ml) MDCK | Vero |
|---|---|---|---|---|---|---|

[1]Measured 72 hours postinoculation
HG = High Growth; P = passages in Vero cells

TABLE 7

Viral Protein Yield of Influenza A/England/1/53 (H1N1) (HG) in Vero and MDCK Cells

| Host System | Material Investigated | Protein Yield[1] (mg) Whole Virus | HA[2] |
|---|---|---|---|
| Vero | Culture fluid | 4.38 | 0.98 |
|  | Cells | 1.25 | 0.36 |
| MDCK | Culture fluid | 4.13 | 1.18 |
|  | Cells | 1.40 | 0.42 |

[1]The concentrated virus was derived from 1 liter of culture fluid or sonicated infected cells; 6.1 × 10$^8$ Vero and 5.8 × 10$^8$ MDCK cells were initially infected.
[2]Quantitation of HA protein was determined by densitometry after polyacrylamide gel electrophoresis.

TABLE 9

Primary Isolation of Influenza A (H3N2) Viruses in Vero Cells During 1993–1994 Epidemic Season

| Strain | HA Titer at 48 and 72 Hours Postinfection in Vero Cells[1] 1st passage 48 | 72 | 2nd passage 48 | 72 | 3rd passage 48 | 72 | Virus Isolation Vero | MDCK[2] | Eggs[3] |
|---|---|---|---|---|---|---|---|---|---|
| A/Mem/1/93 | < | < | 2 | 2 | 8 | 16 | + | + | + |
| A/Mem/1/94 | < | < | < | 4 | 2 | 4 | + | + | + |
| A/Mem/2/94 | < | < | < | 4 | < | 8 | + | + | − |
| A/Mem/7/94 | < | < | 8 | 16 | 8 | 32 | + | + | − |
| Clinical Sample #1 01/12/94 | < | < | < | < | < | < | − | − | − |
| A/Mem/11/94 | < | < | < | 2 | 2 | 16 | + | + | − |
| Clinical Sample #2 01/12/94 | < | < | < | < | < | < | − | − | − |
| A/Mem/12/94 | < | < | < | < | < | < | − | + | − |
| A/Mem/16/94 | < | < | 8 | 16 | 8 | 32 | + | + | − |

< = HA titer less than 1:2, + = virus isolated and typed as influenza A (H3N2), − = virus not isolated
[1]HA titration was performed with 0.4% (v/v) guinea pig erythrocytes
[2]Virus was detected after the first passage in MDCK cells
[3]Virus was detected on the second amniotic passage

TABLE 8

Antigenic Analysis of Influenza A/England/1/53 (HG) Virus Passaged in Vero Cells

| Virus | HI Titers[1] Polyclonal antisera to: A/Eng/53 chick serum | A/WSN/33 rabbit serum | A/FW/1/50 goat serum | A/USSR/90/77 rabbit serum | Anti-HA monoclonal antibodies to: A/Baylor/11515/82 AB-32 | AB-33 | A/Baylor/5700/82 2/6 | 24/1 | 31/1 |
|---|---|---|---|---|---|---|---|---|---|
| A/Eng/53 (HG) | 160 | 100 | 400 | 1600 | 400 | 3200 | 400 | 1600 | 200 |
| A/Eng/53 (2P) | 160 | 100 | 200 | 1600 | 400 | 1600 | 400 | 800 | 200 |
| A/Eng/53 (7P) | 160 | 100 | 400 | 1600 | 200 | 3200 | 400 | 800 | 200 |
| A/Eng/53 (10P) | 320 | 100 | 200 | 1600 | 200 | 3200 | 400 | 1600 | 200 |
| A/Eng/53 (20P) | 320 | 100 | 400 | 1600 | 200 | 3200 | 400 | 1600 | 200 |

HG = High Growth; P = passage in Vero cells
[1]Reciprocal of the highest dilution of antibody inhibiting 4 HA units of virus

TABLE 10

Primary Isolation of Influenza A and B Viruses from Clinical Samples

| | Clinical Samples Yielding:* | | | |
|---|---|---|---|---|
| | Influenza A virus (n = 27) | | Influenza B virus (n = 21) | |
| Cell System | No. of HA positive (%) | Infectivity range ($\log_{10}TCID_{50}$/ml) | No. of HA positive (%) | Infectivity range ($\log_{10}TCID_{50}$/ml) |
| Vero | 19 (70.4) | 2.2–2.7 | 10 (47.6) | 2.0–2.2 |
| MDCK | 20 (74.1) | 2.8–3.1 | 12 (57.1) | 2.7–3.0 |
| Eggs | 4 (14.8) | 2.6–3.0 | 9 (42.9) | 2.0–2.2 |

*HA positivity and $TCID_{50}$ values were determined at 72–96 hr. postinfection after the second passage in the cell system tested.

TABLE 11

Antigenic Analysis of Influenza B/Ann Arbor/1/86 Strain Passaged in Vero cells

| | HI Titer | | | | | | | |
|---|---|---|---|---|---|---|---|---|
| | Polyclonal antisera to: | | | Anti-HA monoclonal antibodies to: | | | | |
| | | | | B/Hong Kong/8/73 | | | B/Ann Arbor/1/86 | |
| Virus | B/Vic/70 | B/HK/73 | B/AA/86 | 82/1 | 419/2 | 430/1 | 1/1 | 1/2 |
| B/AA/86(1P) | 80 | 86 | 160 | 160 | 320 | 160 | 800 | 1600 |
| B/AA/86(20P) | 160 | 80 | 160 | 160 | 320 | 320 | 800 | 1600 |

TABLE 12

Sequence Analysis of the HA1 Region of the Hemagglutinin of Influenza B Viruses Isolated and Passaged in Different Host Systems

| | Culture System | | Amino Acid Position |
|---|---|---|---|
| Virus | Isolation | Passage Number | 196–198[1] |
| B/Ann Arbor/1/86 | Eggs | Eggs (n)[2] | Asp—Thr |
| | | Vero (20) | Asp—Thr |
| B/Memphis/1/93 | Eggs | Eggs (n) | Asn—Ala |
| | | Vero (10) | Asn—Ala |
| | MDCK | MDCK (1) | Asn—Thr |
| | | MDCK (3) | Asn—Thr |
| | Vero | Vero (1) | Asn—Thr |
| | | Vero (4) | Asn—Thr |

[1] All nucleotide changes were restricted to codons for residues 196–198 within the HA1 region of each virus.
[2] n = numerous passages in eggs.

TABLE 13

Efficiency of Influenza A and B Virus Infection of Vero and MDCK Cells

| | % Cell Expressing HA at 6 hr. postinfection at different m.o.i.'s | | | | | |
|---|---|---|---|---|---|---|
| Cell System | A/England/1/53 (H1N1) | | | B/Ann Arbor/1/86 | | |
| moi | .1 | 1.0 | 10 | .1 | 1.0 | 10 |
| Vero | 2.9 | 45.2 | 87.1 | 1.7 | 16.7 | 81.2 |
| MDCK | 8.7 | 45.4 | 91.0 | 2.6 | 25.7 | 85.1 |

TABLE 14

Relative Amounts of Influenza A and B Viral Proteins Synthesized in Vero and MDCK Cells*

Frequency Distribution of Proteins in Host Cells (%)*

| A/England/1/53 (H1N1) | | | B/Ann Arbor/1/86 | | |
|---|---|---|---|---|---|
| Protein | Vero | MDCK | Protein | Vero | MDCK |
| HA | 32.6 | 22.1 | HA | 19.5 | 22.6 |
| NP | 34.1 | 33.2 | NP | 38.9 | 43.2 |
| M1/NS1 | 21.8 | 31.4 | M1 | 16.4 | 13.8 |
| M2 | 5.8 | 6.9 | NS1 | 25.2 | 20.4 |
| NS2 | 5.7 | 6.4 | NS2 | ND | ND |

*The percentage of each influenza virus protein was calculated according to the intensity of the band on a 15% SDS-PAGE gel; the intensity of all bands was taken as 100%.
ND = Not done.

References

Air et al., *Structure, Function, and Genetics* 6:341–356 (1989)

*Avery's Drug Treatment: Principles and Practice of Clinical Pharmacology and Therapeutics,* 3rd edition, ADIS Press, LTD., Williams and Wilkins, Baltimore, Md. (1987)

Barrett et al, *Virology: A Practical Approach*, Oxford IRL Press, Oxford (1985) pp. 119–150

Baum & Paulson, *Acta Histochem. Suppl.* 40:35–38 (1990)

Berkow et al., eds., *The Merck Manual*, 15th edition, Merck and Co., Rahway, N.J. (1987)

Demidova et al., *Vopr. Virosol* (Russian) 346–352 (1979)

Dochmer, *Dev. Biol. Stand.* 68:33 (1987)

Ebadi, *Pharmacology*, Little, Brown and Co., Boston, Mass. (1985)

Edwards, *J. Infect. Dis.* 169:68–76 (1994)

Ewami et al., *Proc. Natl. Acad. Sci. USA* 87:3802–3805 (1990)

Frank et al., *J. Clin. Microb.* 10:32–36(1979)

Goodman et al., eds., *Goodman and Gilman's The Pharmacological Basis of Therapeutics*, 8th edition, Pergamon Press, Inc., Elmsford, N.Y. (1990)

Govorkova et al., *J. Infect. Dis.* 172:250–253 (1995)

Grachev et al., *In Guidance for the Production of Vaccines and Sera*, Burgamov, ed., Medicine, Moscow (1978), p. 176

Grachev, In *Zh. Microbiol. Epidemiol. Immunobiol.* 2:76 (1987)

Gubareva et al., *Virol.* 199:89–97 (1994)

Hayden, F. G. et al., *Antimicrob. Agents Chemother.* 17:865–870 (1980)

Hinshaw, V. S. et al., *J. Virol.* 68:3667–3673 (1994)

Itoh et al *Virus* 18:214–226 (1968)

Itoh et al., *Japan. J. Mol. Sci. Biol.* 23:227–235 (1970)

Johnson et al, *J. Cancer* 24:27 (1979)

Karber, *Arch. Exp. Path. Pharmak.* 162:480–483 (1931)

Katz & Webster, *J. Gen. Virol.* 73:1159–1165(1992)

Katz & Webster, *J. Infect Dis.* 160:191–198 (1989)

Katz et al., *J. Infect. Dis.* 160:191–198 (1989)

Katz et al., *J. Virol.* 64:1808–1811 (1990)

Katz et al., *Virology* 156:386–395 (1987)

Katz et al., *Virology* 165:446–456 (1988)

Monto, et al., *J. Clin. Microb.* 13:233–235 (1981)

Murphy, *Infect. Dis. Clin. Pract.* 2:174–181 (1993)

Muster et al., *Proc. Natl. Acad. Sci. USA* 88:5177–5181 (1991)

Nakamura et a., *J. Gen. Virol.* 56:199–202 (1981)

Ogra et al., *J. Infect. Dis.* 135:499–506 (1977)

Osol, ed., *Remington's Pharmaceutical Sciences*, Mack Publishing Co, Easton, Pa. (1980), pp. 1324–1341

Oxford et al., *Arch. Virol.* 110:37–46 (1990)

Oxford et al., *J. Gen. Virol.* 72:185–189 (1991)

Robertson et al., *Biologicals* 20:213–220 (1992)

Robertson et al, *Giornale di Igiene e Medicina Preventiva* 29:4–58 (1988)

Robertson et al., *Virology* 143:166–174 (1985)

Robertson et al., *Virology* 179:35–40 (1990)

Sanger et al., Proc. *Natl. Acad. Sci. USA* 74:5463–5467 (1977)

Schepetink & Kok, *J. Virol Methods* 42:241–250 (1993)

Smith et al., *J. Clin. Microbiol.* 24:265 (1986)

Subbarao et al., *J. Virol.* 67:7223–7228 (1993)

Takizawa et al., *J. Gen. Virol.* 74:2347–2355 (1993)

Valette et al., *Antimicrobiol. Agent and Chemotherapy* 37:2239–2240 (1993)

Wharton et al., in *The Influenza Viruses*, R. M. Krug, ed., Plenum Press, New York (1989), pp. 153–174

Wood et al., *Virol.* 171:214–221 (1989)

Wyllie et al., *Inter. Rev. Cytol.* 68:251–306 (1980)

Zuckerman et al., *J. Infect. Dis.* 28:41–48 (1994)

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

A G C G A A A G C A  G G     1 2

---

Katzung, ed. *Basic and Clinical Pharmacology*, Fifth Edition, Appleton and Lange, Norwalk, Conn. (1992)

Kaverin & Webster, *J. Virol.* 69:2700–2703 (1995)

Kendal et al., *Infect. Immun.* 29:966–971 (1980)

Kerr et al., *Lancet* 1:291–295 (1975)

Kilbourne, *Bull. M2 World Health Org.* 41:643–645 (1969)

Köhler & Milstein, *Eur. J Immunol.* 6:511–519 (1976)

Kodihalli et al., *J. Virol.* 69:4888–4897 (1995)

Krug et al., *The Influenza Viruses*, Krug, R. M., ed., Plenum Press, New York (1989), pp. 89–152

Lau & Scholtissek, *Virology* 212:225–231 (1995)

Levinson et al., In *Abnormal Cells, New Products and Risk*, Hopps et al., Tissue Culture Association, Galihesbury (1985), p. 161

Mahy et al., *J. Biol. Stand.* 5:237–247 (1977)

Mizrahi, ed., *Viral Vaccines*, Wiley-Liss, New York (1990)

Montagnon et al., *Dev. Biol Stand.* 47:55 (1987)

What is claimed is:

1. A method for replicating at least one high growth strain of a passaged clinical isolate, or reassortant, derived from at least one naturally occuring mammalian influenza virus strain, comprising (a) infecting cultured primary mammalian cells with said high growth strain of said passaged clinical isolate or said reassortant to obtain infected cells; and (b) culturing said infected cells in the presence of trypsin at a continuous concentration range of 0.05–1.0 μg/ml in the culture medium during the influenza virus growth cycle, to obtain replicated mammalian influenza virus, wherein (i) when said passaged clinical isolates are used to provide said high growth strain, the passaged clinical isolates have not been passaged in avian eggs; and (ii) said cultured mammalian cells lack adventitous agents to the extent that said cells are suitable to be certified for mammalian virus vaccine production.

2. The method of claim 1, wherein the multiplicity of virus infection of said isolate or said reassortant is $5\times10^{-6}$ to $5\times10^{-3}$ $TCID_{50}$, said $TCID_{50}$ being the tissue culture infective dose sufficient to infect about 50% of the cultured cells per cell.

3. The method of claim 1, wherein the multiplicity of infection of said isolates or reassortants is between $1\times10^{-6}$ and $1\times10^{-5}$ $TCID_{50}$ per cell.

4. The method of claim 1, wherein the trypsin is added at intervals in the culture medium to maintain said trypsin concentration range during the viral growth cycle.

5. The method of claim 1, wherein the trypsin is continuously added to the culture medium to maintain said trypsin concentration range during the viral growth cycle.

6. The method of claim 5, wherein the concentration of trypsin is maintained between 0.5 and 0.9 $\mu$g/ml during the viral growth cycle.

7. The method of claim 1, wherein the mammalian influenza virus is a strain of mammalian influenza A virus.

8. The method of claim 1, wherein the mammalian influenza virus is a strain of human influenza B virus.

9. The method of claim 1, wherein said cultured mammalian cells are cultured primary epithelial cells or fibroblast cells.

10. The method of claim 9, wherein said cultured primary epithelial cells are Vero cells.

11. The method of claim 10, wherein said Vero cells have a passage number of 20–190.

12. The method of claim 1, wherein said mammalian influenza virus is a human influenza virus.

* * * * *